United States Patent
Klaus et al.

(10) Patent No.: US 7,354,931 B2
(45) Date of Patent: Apr. 8, 2008

(54) HETEROCYCLIC RETINOID COMPOUNDS

(75) Inventors: Michael Klaus, Weil am Rhein (DE); Jean-Marc Lapierre, Pelham, NH (US)

(73) Assignee: Roche Palo Alto LLC, Palo Alto, CA (US)

( * ) Notice: Subject to any disclaimer, the term of this patent is extended or adjusted under 35 U.S.C. 154(b) by 148 days.

(21) Appl. No.: 10/960,372

(22) Filed: Oct. 7, 2004

(65) Prior Publication Data
US 2005/0049238 A1 Mar. 3, 2005

Related U.S. Application Data

(62) Division of application No. 10/283,841, filed on Oct. 30, 2002, now Pat. No. 6,818,652.

(60) Provisional application No. 60/335,129, filed on Oct. 31, 2001.

(51) Int. Cl.
*C07D 251/02* (2006.01)
*A61K 31/47* (2006.01)
(52) U.S. Cl. .................. 514/311; 546/156; 546/139
(58) Field of Classification Search ................ 514/311; 546/156, 139
See application file for complete search history.

(56) References Cited

U.S. PATENT DOCUMENTS 5,716,624 A 2/1998 Bernardon 6,046,220 A 4/2000 Bernardon

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
West, Anthony R., Solid State Chemistry and its Applications, Wiley, New York, 1988, pp. 358 & 365.*
Barnes, Novel Approaches and Targets for Treatment of Chronic Obstructive Pulmonary Disease, Am J Respir Crit Care Med vol. 160, pp. S72-S79, 1999.*
Mao, A Pilot Study of All-trans-Retinoic Acid for the Treatment of Human Emphysema, Am J Respir Crit Care Med vol. 165. pp. 718-723, 2002.*
Fujita, Retinoic acid fails to reverse emphysema in adult mouse models, Thorax 2004; 59:224-230.*
. . . Dorwald F. A. Side Reactions in Organic Synthesis, 2005, Wiley: VCH, Weinheim p. IX of Preface.*

* cited by examiner

*Primary Examiner*—Rita Desai
(74) *Attorney, Agent, or Firm*—Brian L. Buckwalter

(57) ABSTRACT

The current invention provide novel heterocyclic retinoid compounds, methods of treating or preventing chronic obstructive pulmonary disease, cancer and dermatological disorders, pharmaceutical compositions suitable for the treatment or prevention of these disorders and methods for delivering formulations of these retinoids to a mammal having these disorders.

2 Claims, No Drawings

HETEROCYCLIC RETINOID COMPOUNDS

CROSS-REFERENCE TO RELATED APPLICATION

This application is a divisional application of U.S. Ser. No. 10/283,841, filed Oct. 30, 2002 now U.S. Pat. No. 6,818,652 which claims the benefit under 35 U.S.C. 119(e) of U.S. Provisional Application Ser. No. 60/335,129, filed Oct. 31, 2001. Both applications hereby incorporated by reference in its entirety.

1. FIELD OF THE INVENTION

The invention relates to novel heterocyclic retinoid compounds and methods of synthesis thereof. The invention also relates to methods of using these heterocyclic retinoid compounds and pharmaceutical compositions thereof.

2. BACKGROUND OF THE INVENTION

2.1. Retinoids

The retinoids are structural analogues of vitamin A and include both natural and synthetic compounds. Retinoid compounds such as all trans retinoic acid ("ATRA"), 9-cis-retinoic acid, trans 3-4 didehydroretinoic acid, 4-oxo retinoic acid, 13-cis-retinoic acid and retinol are pleiotrophic regulatory compounds that influence a large number of inflammatory, immune and structural cells.

For example, retinoids modulate epithelial cell proliferation, morphogenesis in lung and differentiation through a series of hormone nuclear receptors that belong to the steroid/thyroid receptor superfamily. The retinoid receptors are classified into the retinoic acid receptors (RAR) and the retinoid X receptors (RXR) each of which consists of three distinct subtypes ($\alpha$, $\beta$ and $\gamma$).

ATRA is the natural ligand for the retinoic acid receptors and binds with similar affinity to the $\alpha$, $\beta$ and $\gamma$ subtypes. A quantitative structure-activity relationship has been established for a number of synthetic RAR $\alpha$, $\beta$ and $\gamma$ retinoid agonists, which has elucidated the principal electronic and structural characteristics that provide selective affinity for each RAR subtype (Douget et al., *Quant. Struct. Act. Relat.*, 18, 107, 1999).

ATRA does not bind to RXR, for which 9-cis-retinoic acid is the natural ligand. A number of synthetic RXR and RAR $\alpha$, $\beta$ and $\gamma$ retinoid agonists have also been described in the art (See, e.g., Billoni et al., U.S. Pat. No. 5,962,508; Belloni et al., WO 01/30326, published May 3, 2001; Klaus et al., U.S. Pat. No. 5,986,131; and Bernardon et al., WO92/06948, published 30 Apr. 1992). Other retinoid patents include Bernadon, U.S. Pat. Nos. 5,716,624 and 6,046,220.

2.2. Therapeutic Uses of Retinoids in Dermatology and Cancer

In tissues other than pulmonary tissues, retinoids typically have anti-inflammatory effects, can alter the progression of epithelial cell differentiation and may inhibit stromal cell matrix production. These biological effects of retinoids have led to the development of many topical agents for dermatological disorders such as psoriasis, acne and hypertrophic cutaneous scars. Retinoids have also been used in the treatment of light and age damaged skin, the healing of wounds caused, for example, by surgery and burns (Mustoe et al., *Science* 237, 1333 1987; Sprugel et al., *J. Pathol.*, 129, 601, 1987; Boyd, *Am. J. Med.*, 86, 568, 1989) and as anti-inflammatory agents for treatment of arthritis. Other medicinal applications of retinoids include the control of acute promyelocytic leukemia, adeno and squamous cell carcinoma and hepatic fibrosis. Retinoids have also been used extensively in treatment of premalignant epithelial lesions and malignant tumors (carcinomas) of epithelial origin (Bollag et al., U.S. Pat. No. 5,248,071; Sporn et al., *Fed. Proc.* 1976, 1332; Hong et al., "Retinoids and Human Cancer" in *The Retinoids: Biology, Chemistry and Medicine*, M. B. Sporn, A. B. Roberts and D. S. Goodman (eds.) Raven Press, New York, 1994, 597-630). However, many known retinoids lack selectivity and consequently exert harmful pleiotrophic effects that may cause patient death when used in therapeutically effective amounts. Thus, the therapeutic use of retinoids in diseases other then cancer has been limited by toxic side effects. A general review of retinoids can be found in Goodman & Gilman's "The Pharmacological Basis of Therapeutics", Chapters 63-64, $9^{th}$ edition, 1996, McGraw-Hill.

2.3. Emphysema

Chronic Obstructive Pulmonary Disease ("COPD") refers to a large group of lung diseases which prevent normal respiration. Approximately 11% of the population of the United States has COPD and available data suggests that the incidence of COPD is increasing. Currently, COPD is the fourth leading cause of mortality in the United States.

COPD is a disease in which the lungs are obstructed due to the presence of at least one disease selected from asthma, emphysema and chronic bronchitis. The term COPD was introduced because these conditions often co-exist and in individual cases it may be difficult to ascertain which disease is responsible for causing the lung obstruction (1987 Merck Manual). Clinically, COPD is diagnosed by reduced expiratory flow from the lungs that is constant over several months and in the case of chronic bronchitis persists for two or more consecutive years. The most severe manifestations of COPD typically include symptoms characteristic of emphysema.

Emphysema is a disease where the gas-exchange structures (e.g., alveoli) of the lung are destroyed, which causes inadequate oxygenation that may lead to disability and death. Anatomically, emphysema is defined by permanent airspace enlargement distal to terminal bronchioles (e.g., breathing tubes) which is characterized by reduced lung elasticity, decreased alveolar surface area and gas exchange and alveolar destruction that results in decreased respiration. Thus, the characteristic physiological abnormalities of emphysema are reduced gas exchange and expiratory gas flow.

Cigarette smoking is the most common cause of emphysema although other environmental toxins may also contribute to alveoli destruction. The injurious compounds present in these harmful agents can activate destructive processes that include, for example, the release of excessive amounts of proteases that overwhelm normal protective mechanisms, such as protease inhibitors present in the lung. The imbalance between proteases and protease inhibitors present in the lung may lead to elastin matrix destruction, elastic recoil loss, tissue damage, and continuous lung function decline. The rate of lung damage may be decreased by reducing the amounts of toxins in the lung (i.e., by quitting smoking). However, the damaged alveolar structures are not repaired and lung function is not regained. At least four different types of emphysema have been described according to their locations in the secondary lobule: panlobar emphysema, centrilobular emphysema, distal lobular emphysema and paracicatrical emphysema.

The major symptom of emphysema is chronic shortness of breath. Other important symptoms of emphysema include, but are not limited to, chronic cough, coloration of the skin caused by lack of oxygen, shortness of breath with minimal physical activity and wheezing. Additional symptoms that may be associated with emphysema include but are not limited to vision abnormalities, dizziness, temporary cessation of respiration, anxiety, swelling, fatigue, insomnia and memory loss. Emphysema is typically diagnosed by a physical examination that shows decreased and abnormal breathing sounds, wheezing and prolonged exhalation. Pulmonary function tests, reduced oxygen levels in the blood and a chest X-ray may be used to confirm a diagnosis of emphysema.

No effective methods for reversing the clinical indications of emphysema currently exist in the art. In some instances, medications such as bronchodilators, β-agonists, theophylline, anticholinergics, diuretics and corticosteroids delivered to the lung by an inhaler or nebulizer may improve respiration impaired by emphysema. Oxygen treatment is frequently used in situations where lung function has been so severely impaired that sufficient oxygen cannot be absorbed from the air. Lung reduction surgery may be used to treat patients with severe emphysema Here, damaged portions of the lung are removed, which allows the normal portions of the lung to expand more fully and benefit from increased aeration. Finally, lung transplantation is another surgical alternative available to individuals with emphysema, which may increase quality of life but does not significantly improve life expectancy.

2.4. Lung Development, Alveolar Septation and Use of Retinoids in Treating Emphysema Alveoli are formed during development by division of saccules that constitute the gas-exchange elements of the immature lung. The precise mechanisms governing formation of septa and their spacing remain currently unknown in primates. Retinoids such as ATRA, which is a multifunctional modulator of cellular behavior that may alter both extracellular matrix metabolism and normal epithelial differentiation, have a critical regulatory role in mammals such as the rat. For example, ATRA modulates critical aspects of lung differentiation through binding to specific retinoic acid receptors that are selectively temporally and spatially expressed. Coordinated activation of different retinoic acid receptors subtypes has been associated with lung branching, alveolization/septation and gene activation of tropoelastin in neonatal rats.

During alveolar septation, retinoic acid storage granules increase in the fibroblastic mesenchyme surrounding alveolar walls (Liu et al., *Am. J. Physiol.* 1993, 265, LA30; McGowan et al., *Am. J. Physiol.*, 1995, 269, LA63) and retinoic acid receptor expression in the lung peaks (Ong et al., *Proc. Natl. Acad. of Sci.*, 1976, 73, 3976; Grummer et al., *Pediatr. Pulm.* 1994, 17, 234). The deposition of new elastin matrix and septation parallels depletion of these retinoic acid storage granules. Postnatal administration of retinoic acid has been shown to increase the number of alveoli in rats, which supports the concept that ATRA and other retinoids may induces alveoli formation (Massaro et al., *Am. J. Physiol.*, 270, L305, 1996). Treatment of newborn rat pups with dexamethasone, a glucocorticosteroid, prevents septation and decreases expression of some sub-types of retinoic acid receptor. Supplemental amounts of ATRA have been shown to prevent dexamethasone inhibition of alveoli formation. Further, ATRA prevents dexamethasone from diminishing retinoic acid receptor expression and subsequent alveolar septation in developing rat lung.

ATRA has been reported to induce formation of new alveoli and returns elastic recoil in the lung to approximately normal values in animal models of emphysema (Massaro et al., *Nature Med.*, 1997, 3, 675; "Strategies to Augment Alveolization," National Heart, Lung, and Blood Institute, RFA: HL-98-011, 1998; Massaro et al., U.S. Pat. No. 5,998,486). However, the mechanism of action of ATRA in these studies remains undefined, although Massaro reports that ATRA generates new alveoli. More importantly, the use of ATRA presents several toxicity or adverse effects concerns.

Thus, novel retinoid agonists useful for treating dermatological disorders, disorders of the lung such as COPD, emphysema and cancer without the toxicity problems of ATRA or other retinoids are highly desirable.

3. SUMMARY OF THE INVENTION

The current invention provides novel heterocyclic retinoid compounds, methods of treating or preventing disorders of the lung such as chronic obstructive airway disorders, cancer and dermatological disorders, pharmaceutical compositions suitable for the treatment or prevention of such diseases or disorders and methods for delivering formulations of novel heterocyclic retinoid compounds into the lung of a mammal suffering from such diseases or disorders.

In one embodiment, the present invention provides compounds according to structural formula (I):

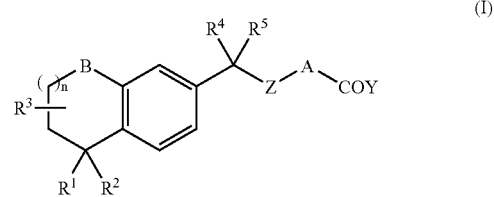

(I)

or a pharmaceutically acceptable salt, solvate or hydrate thereof wherein:

n is an integer from 0 to 2;

A is aryl or heteroaryl;

B is O, S or $NR^6$;

$R^6$ is hydrogen or alkyl;

Y is $-OR^7$, $-SR^7$ or $-NR^8R^9$;

$R^7$ is hydrogen, alkyl, aryl, arylalkyl, cycloalkyl or cycloalkyl-alkyl;

$R^8$ and $R^9$ are independently hydrogen, alkyl, aryl, arylalkyl, cycloalkyl or cycloalkyl-alkyl or together with the nitrogen atom to which they are attached form a heterocycloamino ring;

Z is $-C(R^{101})_2O-$, $-R^{102}C=CR^{102}-$, $-C\equiv C-$, $-C(R^{103})_2S-$, $-C(O)O-$ or $-C(O)NR^{10}-$;

each of $R^{10}$, $R^{101}$, $R^{102}$ and $R^{103}$ is independently hydrogen or alkyl;

$R^1$ and $R^2$ are independently hydrogen or alkyl;

$R^3$ is hydrogen, alkyl; and $R^4$ and $R^5$ are independently hydrogen, $(C_1-C_8)$alkyl or arylalkyl.

The present invention encompasses the use of the compounds of the invention to treat or prevent certain chronic obstructive airway disorders, particularly chronic obstructive pulmonary disease including chronic bronchitis, emphysema and asthma in mammals, especially humans that smoke or smoked cigarettes. In a preferred embodiment, the invention encompasses the treatment or prevention of panlobar emphysema, centrilobular emphysema or distal lobular emphysema in mammals using non-toxic and therapeutically effective doses of the compounds of the invention.

The present invention also encompasses the use of the compounds of the invention for treating or preventing cancer or dermatological disorders. Further, the instant invention encompasses the use of pharmaceutical compositions of the compounds of the invention to treat or prevent chronic obstructive airway disorders, cancer or dermatological disorders. Moreover, the invention encompasses the use of electrohydrodynamic aerosol devices, aerosol devices and nebulizers to deliver formulations of compounds of the invention into the lung of a mammal suffering from or at risk of chronic obstructive airway disorders or cancer.

The invention also encompasses the systemic use as well as the local use of the compounds of the invention or both in combination. Either or both can be achieved by the oral, mucosal or parenteral modes of administration. As mentioned above, means of delivering compounds of the invention directly into the lung by nebulizer, inhaler or other known delivery devices are encompassed by the invention. A method for treatingchronic obstructive airway disorders, cancer or dermatological disorders by combining compounds of the invention with one or more additional therapies is also encompassed by the invention.

4. DETAILED DESCRIPTION OF THE INVENTION

4.1 Definitions

As used herein the term "compounds of the invention" means the compounds of generic formula (I) including but not limited to specific compounds within those formulas disclosed herein. The compounds of the invention are identified herein by their chemical structure and/or chemical name. Where a compound is referred to by both a chemical structure and a chemical name and the chemical structure and chemical name conflict, the chemical structure is determinative of the compound's identity. The compounds of the invention may contain one or more chiral centers and/or double bonds and therefore, may exist as stereoisomers, such as double-bond isomers (i.e., geometric isomers), enantiomers, or diastereomers. According to the invention, the chemical structures depicted herein, and therefore the compounds of the invention, encompass all of the corresponding compound's enantiomers and stereoisomers, that is, the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers using either separation techniques or chiral synthesis techniques known in the art.

"Acyl" means a radical —C(O)R, where R is hydrogen, alkyl, cycloalkyl, cycloalkyl-alkyl, aryl or arylalkyl wherein alkyl, cycloalkyl, cycloalkyl-alkyl, aryl and arylalkyl are as defined herein. Representative examples include, but are not limited to formyl, acetyl, cylcohexylcarbonyl, cyclohexylmethylcarbonyl, benzoyl, benzylcarbonyl, and the like.

"Acylamino" means a radical —NR'C(O)R, where R' is hydrogen or alkyl, and R is hydrogen, alkyl, cycloalkyl, cycloalkyl-alkyl, aryl or arylalkyl wherein alkyl, cycloalkyl, cycloalkyl-alkyl, aryl and arylalkyl are as defined herein. Representative examples include, but are not limited to formylamino, acetylamino, cylcohexylcarbonylamino, cyclohexylmethyl-carbonylamino, benzoylamino, benzylcarbonylamino, and the like.

"Alkoxy" means a radical —OR where R represents an alkyl group as defined herein e.g., methoxy, ethoxy, propoxy, butoxy and the like.

"Alkoxycarbonyl" means a radical —C(O)-alkoxy where alkoxy is as defined herein.

"Alkyl" means a linear saturated monovalent hydrocarbon radical of one to eight carbon atoms or a branched saturated monovalent hydrocarbon radical of three to eight carbon atoms, e.g., methyl, ethyl, propyl, 2-propyl, n-butyl, iso-butyl, tert-butyl, pentyl, and the like.

"Alkylamino" means a radical —NHR where R represents an alkyl, cycloalkyl or cycloalkyl-alkyl group as defined herein. Representative examples include, but are not limited to methylamino, ethylamino, isopropylamino, cyclohexylamino, and the like.

"Alkylene" means a linear saturated divalent hydrocarbon radical of one to ten carbon atoms or a branched saturated divalent hydrocarbon radical of three to ten carbon atoms, e.g., methylene, ethylene, 2,2-dimethylethylene, propylene, 2-methylpropylene, butylene, pentylene, and the like.

"Alkylsulfonyl" means a radical —S(O)$_2$R where R is an alkyl, cycloalkyl or cycloalkyl-alkyl group as defined herein, e.g., methylsulfonyl, ethylsulfonyl, propylsulfonyl, butylsulfonyl and the like.

"Alkylsulfinyl" means a radical —S(O)R where R is an alkyl, cycloalkyl or cycloalkyl-alkyl group as defined herein e.g., methylsulfinyl, ethylsulfinyl, propylsulfinyl, butylsulfinyl and the like.

"Alkylthio" means a radical —SR where R is an alkyl, cycloalkyl or cycloalkyl-alkyl group as defined herein e.g., methylthio, ethylthio, propylthio, butylthio, and the like.

"Aryl" means a monocyclic or bicyclic aromatic hydrocarbon radical which is optionally substituted with one or more substituents, preferably one, two or three, substituents preferably selected from the group consisting of acyl, alkyl, acylamino, alkoxycarbonyl, alkyamino, alkylsulfinyl, alkylsulfonyl, alkylthio, alkoxy, amino, carbamoyl, cyano, dialkylamino, ethylenedioxy, halo, haloalkyl, heteroalkyl, hydroxy, hydroxyalkyl, methylenedioxy, nitro and thio. More specifically the term aryl includes, but is not limited to, phenyl, chlorophenyl, fluorophenyl, methoxyphenyl, 1-naphthyl, 2-naphthyl and the derivatives thereof.

"Arylalkyl" refers to an alkyl radical as defined herein in which one of the hydrogen atoms of the alkyl group is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like.

"Aryloxy" means an —O-aryl group where aryl is as defined herein.

"Arylalkyloxy" means an —O-arylalkyl group where arylalkyl is as defined herein.

"Carbamoyl" means the radical —C(O)N(R)$_2$ where each R group is independently hydrogen or alkyl as defined herein.

"Carboxy" means the radical —C(O)OH.

"Cyano" means the radical —CN.

"Cycloalkyl" refers to a saturated monovalent cyclic hydrocarbon radical of three to seven ring carbons e.g., cyclopropyl, cyclobutyl, cyclohexyl, 4-methylcyclohexyl and the like.

"Cycloalkyl-alkyl" means a radical —$R^aR^b$ where $R^a$ is an alkylene group and $R^b$ is a cycloalkyl group as defined herein, e.g., cyclohexylmethyl and the like.

"Dialkylamino" means a radical —NRR' where R and R' independently represent an alkyl, cycloalkyl or cycloalkyl-alkyl group as defined herein. Representative examples include, but are not limited to dimethylamino, methylethylamino, di-(1-methylethyl)amino, (cyclohexyl)(methyl) amino, (cyclohexyl)(ethyl)amino, (cyclohexyl)(propyl) amino, (cyclohexylmethyl)(methyl)amino, (cyclohexylmethyl)(ethyl)amino and the like.

"Halo" means fluoro, chloro, bromo, or iodo, preferably fluoro and chloro.

"Haloalkyl" means an alkyl group substituted with one or more same or different halo atoms, e.g., —$CH_2Cl$, —$CF_3$, —$CH_2CF_3$, —$CH_2CCl_3$ and the like.

"Heteroalkyl" means an alkyl radical as defined herein wherein one or more hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkyl-alkyl; $R^b$ and $R^c$ are independently of each other hydrogen, acyl, alkyl, cycloalkyl, or cycloalkyl-alkyl; and when n is 0, $R^d$ is hydrogen, alkyl, cycloalkyl, or cycloalkyl-alkyl, and when n is 1 or 2, $R^d$ is alkyl, cycloalkyl, cycloalkyl-alkyl, amino, acylamino, alkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, heteroalkyl, halo, hydroxy, alkoxy, nitro, cyano, cycloalkyl, cycloalkylalkyl, —COR (where R is alkyl or optionally substituted phenyl, —$(CR'R'')_n$—COOR (where n is an integer from 0 to 5, R' and R" are independently hydrogen or alkyl, and R is hydrogen, alkyl, cycloalkyl or cycloalkylalkyl), or —$CR'R'')_n$—$CONR^aR^b$ (where n is an integer from 0 to 5, R' and R" are independently hydrogen or alkyl, and $R^a$ and $R^b$ are, independently of each other, hydrogen, alkyl, cycloalkyl or cycloalkylalkyl, or $R^a$ and $R^b$ together with the nitrogen atom to which they are attached form a heterocyclyl ring). More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyriridinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

"Heterocycloamino" means a saturated monovalent cyclic group of 4 to 8 ring atoms, wherein at least one ring atom is N and optionally contains one additional ring heteroatom selected from the group consisting of N, O, or $S(O)_n$ (where n is an integer from 0 to 2), the remaining ring atoms being C. The heterocyclyl ring may be optionally substituted independently with one, two, or three substituents selected from alkyl, haloalkyl, heteroalkyl, acyl, halo, nitro, carboxy; cyano, cyanoalkyl, hydroxy, alkoxy, amino, alkylamino or dialkylamino. More specifically the term heterocyclyl includes, but is not limited to, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, and the derivatives thereof.

"Hydroxyalkyl" means an alkyl radical as defined herein, substituted with one or more hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to structural formula (I) in vivo when such prodrug is administered to a mammalian subject. Prodrugs of a compound of structural formula (I) are prepared by modifying one or more functional group(s) present in the compound of structural formula (I) in such a way that the modification(s) may be cleaved in vivo to release the parent compound. Prodrugs include compounds of structural formula (I) wherein a hydroxy, amino, or sulfhydryl group in a compound of structural formula (I) is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylamino carbonyl) of hydroxy functional groups in compounds of structural formula (I) and the like.

"Protecting group" refers to a grouping of atoms that when attached to a reactive group in a molecule masks, reduces or prevents that reactivity. Examples of protecting groups can be found in T. W. Green and P. G. Futs, "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include but are not limited to, those where the hydroxy group is either acylated or alkylated such as benzyl, and trityl ethers as well as alkyl ethers, tetrahydropyranyl ethers, trialkylsilyl ethers and allyl ethers.

As used herein, the term "mammal" includes human. The terms "human" and "patient" are used interchangeably herein.

"Treating" or "treatment" of chronic obstructive pulmonary disorder, emphysema, cancer or a dermatological disorder includes preventing the disease, (i.e., causing at least one of the clinical symptoms of the disease not to develop in a mammal that may be exposed to or predisposed to the disease but does not yet experience or display symptoms of the disease) inhibiting the disease (i.e., arresting or reducing the development of the disease or at least one of the clinical symptoms) or relieving the disease, (i.e., causing regression of the disease or at least one of the clinical symptoms). Preventing or prevention encompasses administration prior to manifestation of the disease or disorder.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Reference will now be made in detail to preferred embodiments of the invention. While the invention will be described in conjunction with preferred embodiments, it should be understood that it is not intended to limit the invention to these preferred embodiments. To the contrary, it is intended to cover alternatives, modifications, and equivalents as may be included within the spirit and scope of the invention as defined by the appended claims.

4.2. Compounds of the Invention

The present invention encompasses novel compounds and the uses of these novel compounds to effectively treat chronic obstructive pulmonary disorder such as emphysema, cancer and dermatological disorders. The invention encompasses treating chronic obstructive pulmonary disorders and related disorders, cancer and dermatological disorders while reducing or avoiding adverse effects associated with natural and synthetic retinoids when used at therapeutic levels. Adverse effects associated with retinoids at therapeutic levels include, but are not limited to, the toxic effects of hypervitaminosis A, such as headache, fever, skin and membrane dryness, bone pain, nausea and vomiting, psychiatric disorders and gastrointestinal disorders.

In one embodiment, the present invention provides compounds having the structural formula (I):

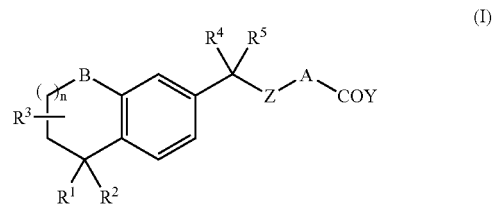

(I)

or a pharmaceutically acceptable salt, solvate or hydrate thereof wherein:
  n is an integer from 0 to 2;
  A is aryl or heteroaryl;
  B is O, S or $NR^6$;
    $R^6$ is hydrogen or alkyl;
  Y is $-OR^7$, $-SR^7$ or $-NR^8R^9$;
    $R^7$ is hydrogen, alkyl, aryl, arylalkyl, cycloalkyl or cycloalkyl-alkyl;
    $R^8$ and $R^9$ are independently hydrogen, alkyl, aryl, arylalkyl, cycloalkyl or cycloalkyl-alkyl or together with the nitrogen atom to which they are attached form a heterocycloamino ring;
  Z is $-C(R^{101})_2O-$, $-R^{102}C=CR^{102}-$, $-C\equiv C-$, $-C(R^{103})_2S-$, $-C(O)O-$ or $-C(O)NR^{10}-$;
    each of $R^{10}$, $R^{101}$, $R^{102}$ and $R^{103}$ is independently hydrogen or alkyl;
  $R^1$ and $R^2$ are independently hydrogen or alkyl;
  $R^3$ is hydrogen or alkyl; and
  $R^4$ and $R^5$ are independently hydrogen, $(C_1-C_8)$alkyl or arylalkyl.

In a preferred embodiment, A has the structural formula (II):

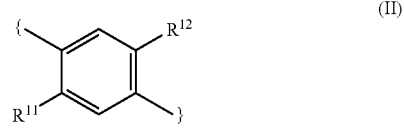

(II)

wherein:
  $R^{11}$ and $R^{12}$ are independently hydrogen, acyl, acylamino, alkoxy, alkoxycarbonyl, alkyl, alkylamino, alkylsulfonyl, alkylsulfinyl, alkylthio, carbamoyl, carboxy, cyano, dialkylamino, halo, haloalkyl, hydroxy, hydroxyalkyl or nitro. In certain embodiments, $R^{11}$ and $R^{12}$ are independently hydroxy, alkoxy, alkyl, haloalkyl, halo or hydrogen. Preferably, $R^{11}$ and $R^{12}$ are hydrogen or in other preferred embodiments $R^{11}$ and $R^{12}$ are different and are either fluorine or hydrogen.

In still another embodiment, Y is $OR^7$ and $R^7$ is hydrogen or methyl, preferably hydrogen.

In another embodiment, n is 1 and $R^3$ is hydrogen.

In still another embodiment, $R^1$ and $R^2$ are alkyl. Preferably, $R^1$ and $R^2$ are methyl.

In preferred embodiments, Z is $-C(R^{101})_2-$, $-R^{102}C=CR^{102}-$, $-C(R^{103})_2S-$, $-C(O)O-$ or $-C(O)NR^{10}-$, and $R^{101}$, $R^{102}$ and $R^{103}$ are hydrogen. More preferably Z is $-CH_2O-$ or trans $-CH=CH-$ In still another embodiment, B is $NR^6$. More preferably $R^6$ is hydrogen, methyl or ethyl. In still another preferred embodiment, B is $NR^6$ and Z is $-CH_2O-$, trans $-HC=CH-$, $-C\equiv C-$, $-C(O)O-$ or $-C(O)NR^{10}-$.

In still another embodiment, $R^4$ is hydrogen. In a preferred embodiment, $R^4$ is hydrogen and $R^5$ is $(C_1-C_8)$alkyl or arylalkyl. Preferably, $R^5$ is ethyl, pentyl, octyl or benzyl. More preferably, $R^5$ is pentyl.

In one preferred embodiment, B is O and Z is $-CH_2O-$ or trans $-HC=CH-$. In another preferred embodiment, B is S and Z is $-CH_2O-$, trans $-HC=CH-$, $-C(O)O-$ or $-C(O)NR^{10}-$.

In another preferred embodiment, n is 1, Y is $OR^7$, $R^1$ and $R^2$ are alkyl, $R^3$ is hydrogen, $R^4$ is hydrogen, $R^5$ is alkyl or arylalkyl, $R^7$ is hydrogen, $R^{11}$ is hydrogen or halo and $R^{12}$ is hydrogen. In a more specific embodiment, B is $NR^6$, Z is $-CH_2O-$, trans $-HC=CH-$ or $-C\equiv C-$, $R^5$ is alkyl and $R^6$ is hydrogen, methyl or ethyl.

Preferred compounds of the invention include those depicted in Table 1 below.

TABLE 1

| Example | Structure | Mass Spec. | M.Pt. |
|---------|-----------|------------|-------|
| 5.1 | 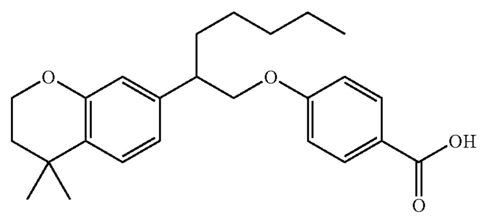 | | 91.5–93.3° C. |
| 5.2 | 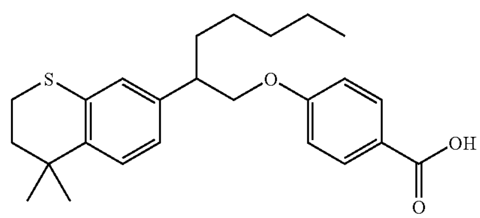 | | 123.0–123.5° C. |
| 5.3 | 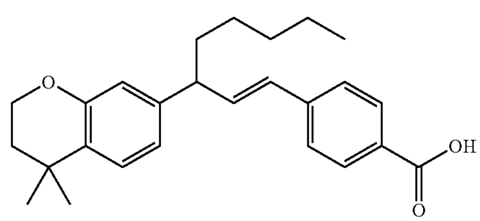 | (M⁻ − 1): 391 | |
| 5.4 | 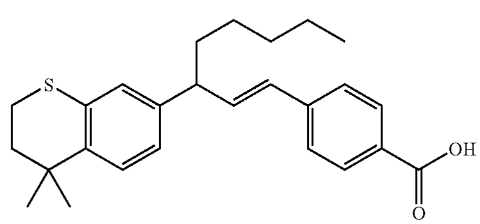 | (M⁻ − 1): 407 | |
| 5.5 | 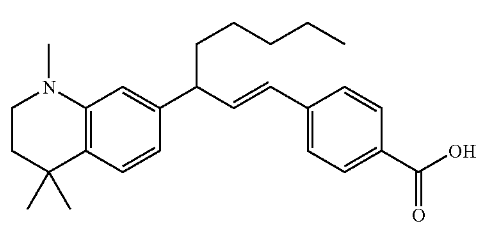 | (M⁺ + 1): 405 | |

TABLE 1-continued
| Example | Structure | Mass Spec. | M.Pt. |
|---|---|---|---|
| 5.6 | 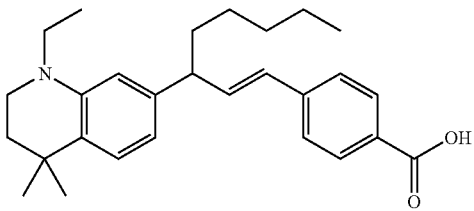 | (M+ + 1): 421 | |
| 5.7 | 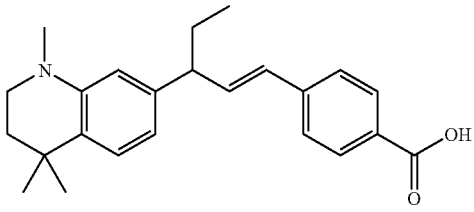 | (M+ + 1): 364 | |
| 5.8 | 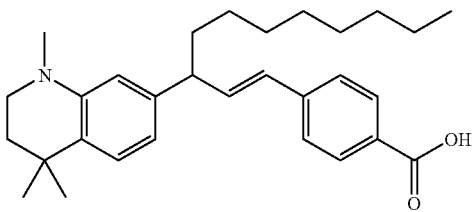 | | |
| 5.9 | 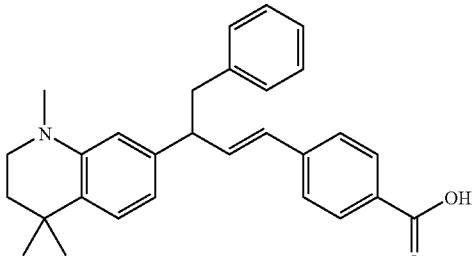 | | |
| 5.10 | 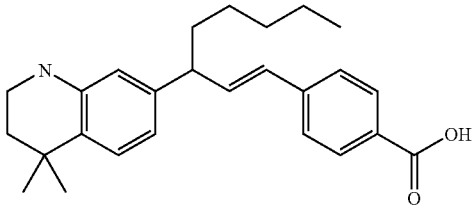 | (M+ + 1): 392 | |
| 5.11 | 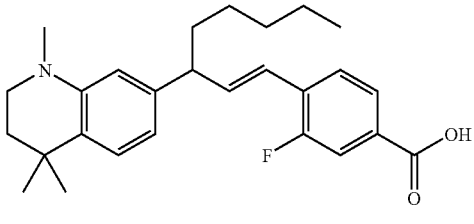 | (M+ + 1): 423 | |

TABLE 1-continued

| Example | Structure | Mass Spec. | M.Pt. |
|---|---|---|---|
| 5.12 | 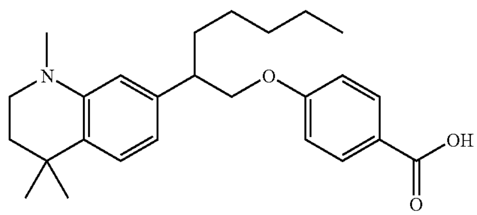 | (M⁺ + 1): 410 | |
| 5.13 | 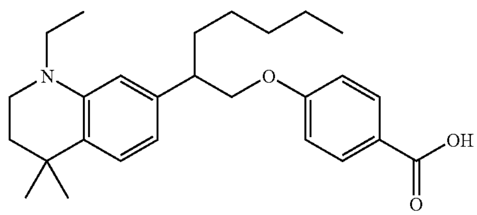 | (M⁺ + 1): 424 | |
| | | | |
| | | | |
| 5.14 | 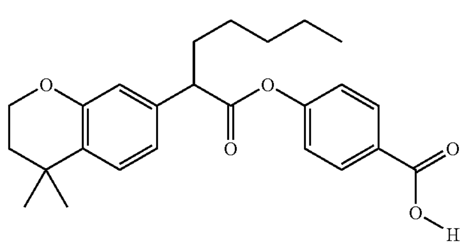 | | |
| 5.15 | 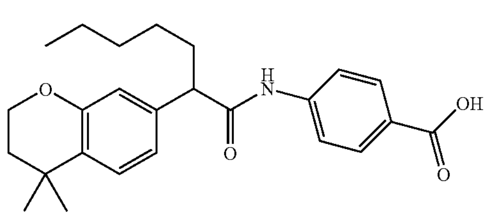 | M⁻: 408 | |

TABLE 1-continued

| Example | Structure | Mass Spec. | M.Pt. |
|---|---|---|---|
| 5.16 | 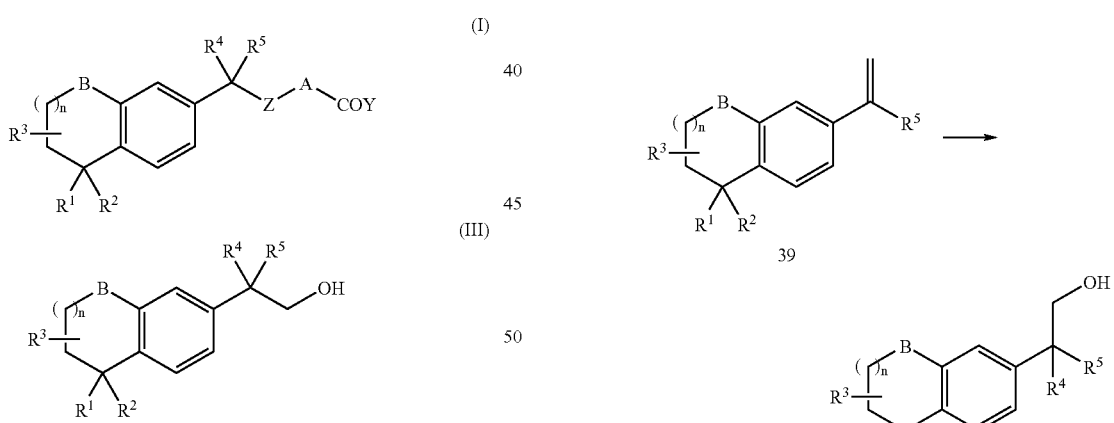 | M−: 388 | |

4.3. Synthesis of the Compounds of the Invention

The compounds of the invention may be obtained via the synthetic methodology illustrated in Schemes 1-6. Starting materials useful for preparing compounds of the invention and intermediates thereof are commercially available or can be prepared by well-known synthetic methods. Methods other than those illustrated in Schemes 1-6 of synthesizing compounds of the invention will be immediately be apparent to those of skill in the art. Accordingly, the synthetic routes presented in Schemes 1-6 are illustrative, rather than comprehensive. Also incorporated by reference is the entire disclosure of copending U.S. patent application Ser. No. 09/840,486 filed Apr. 23, 2001.

Those of skill in the art will recognize that a key intermediate in the synthesis of compounds of Formula (I) is the alcohol of Formula (III) shown below where n, B, $R^1$, $R^2$, $R^3$, $R^4$ and $R^5$ are as defined for Formula (I).

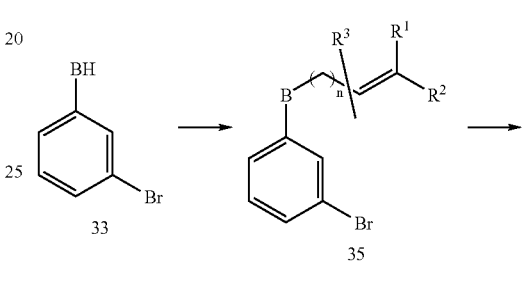

Scheme 1 illustrates a method for synthesizing alcohols of Formula (III) when B is either oxygen or sulfur. Commercially available phenol or thiophenol 33 is converted to alkene 35 or an alkene equivalent (i.e., a tertiary alcohol) by alkylation or Michael addition. Intramolecular Friedel Crafts cyclization (e.g., $AlCl_3$) provides the indan 37. Formation of an organometallic indan derivative (e.g., n-butyl lithium) followed by quenching with a Weinreb amide gives the ketone which may be converted via Wittig chemistry (e.g., methyltriphenylphosphonium halide and base) to alkene 39. Standard hydroboration-oxidation (e.g., diborane, hydrogen peroxide) provides alcohol 41 (B=O or S).

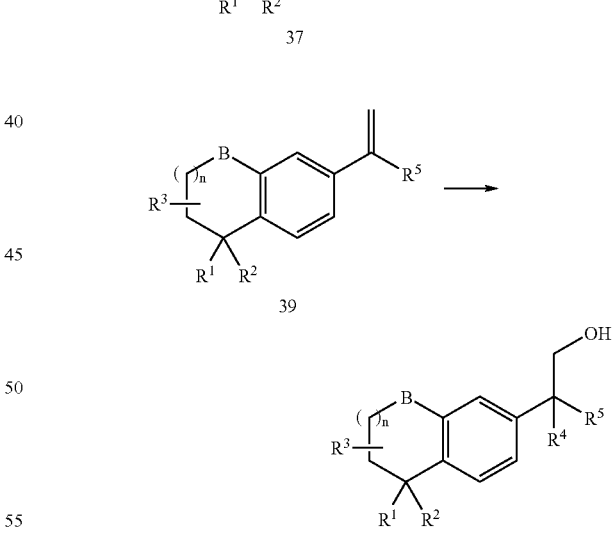

Scheme 2 illustrates preparation of alcohols of Formula (III) when B is nitrogen, i.e., quinoline alcohol derivatives 51. Commercially available 3-nitro phenyl acetic acid is esterified (e.g., Fischer esterification) and alkylated (e.g., cesium carbonate, alkyl halide) to provide nitro ester 45. The nitro group is reduced (e.g., metal catalyst and hydrogen) and acylated to provide alkenyl amide 47, which upon treatment with a Friedel-Crafts catalyst (e.g., $AlCl_3$) undergoes intramolecular cyclization to provide alcohol 51 after reduction of both the ester and amide group (e.g., lithium aluminum hydride). It should be noted that alcohol 51 may be converted to a N-alkyl derivative $NR^6$ by alkylation or reductive alkylation or in the alternative may be protected (i.e., carbamate, thioamide, etc.) if this is necessary for subsequent conversion to compounds of Formula (I).

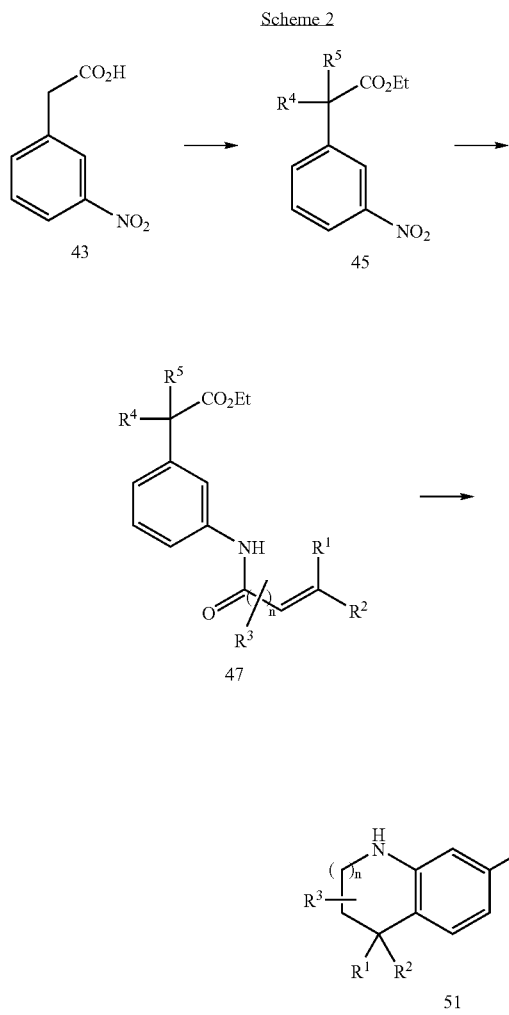

It should be noted in Schemes 3-6 that n, A, B, Y, $R^1$, $R^2$, $R^3$, $R^4$ and $R^5$ are as defined for Formula (I) or are protected precursors thereto. Typically, compounds where Y is $SR^7$ or $NR^8R^9$ are prepared from the precursor acid (Y=OH) by activation of the acid and displacement with the appropriate sulfur or nitrogen nucleophile.

Scheme 3 illustrates conversion of alcohol 53 to a compound of Formula (I), where the linking group Z is an alkene. Preferably, when B=$NR^6$ and $R^6$ is hydrogen the nitrogen atom is protected before commencing the above sequence of steps and deprotected after formation of the olefin (See e.g., Green et al., "Protective Groups in Organic Chemistry", (Wiley, $2^{nd}$ ed. 1991)). Alcohol 53 is oxidized to aldehyde 55 (e.g., pyridinium chlorochromate or Swern oxidation) which is reacted with the phosphonate derivative 57 (e.g., prepared by conventional methods such as displacement of the halide with a trialkylphosphonate) in the presence of base to directly provide derivative 59.

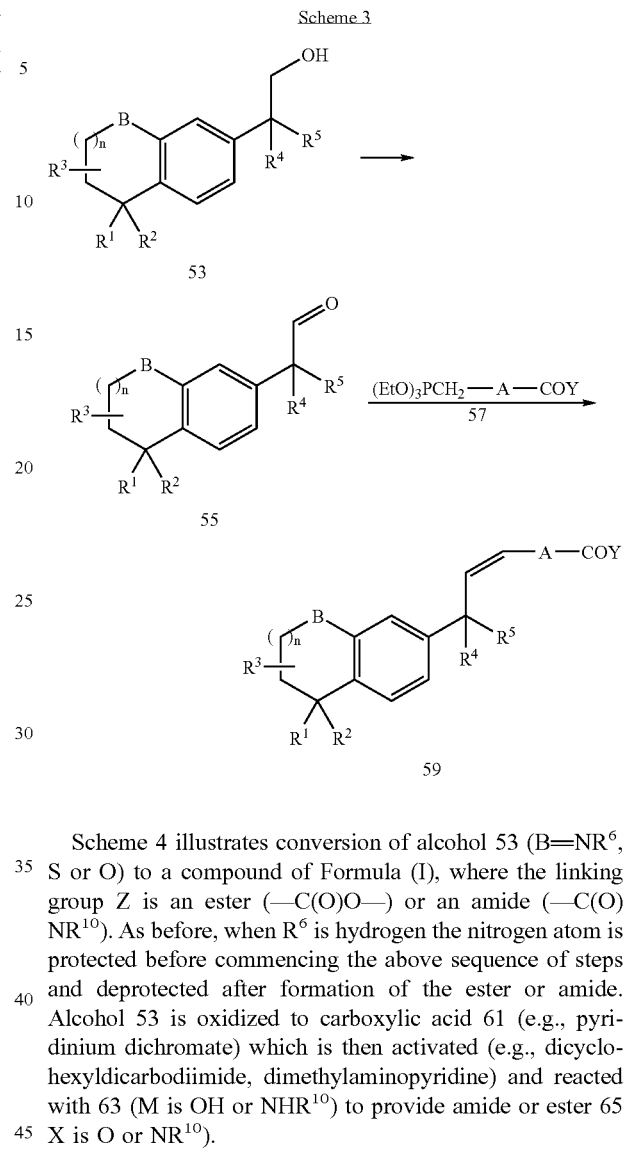

Scheme 4 illustrates conversion of alcohol 53 (B=$NR^6$, S or O) to a compound of Formula (I), where the linking group Z is an ester (—C(O)O—) or an amide (—C(O) $NR^{10}$). As before, when $R^6$ is hydrogen the nitrogen atom is protected before commencing the above sequence of steps and deprotected after formation of the ester or amide. Alcohol 53 is oxidized to carboxylic acid 61 (e.g., pyridinium dichromate) which is then activated (e.g., dicyclohexyldicarbodiimide, dimethylaminopyridine) and reacted with 63 (M is OH or $NHR^{10}$) to provide amide or ester 65 X is O or $NR^{10}$).

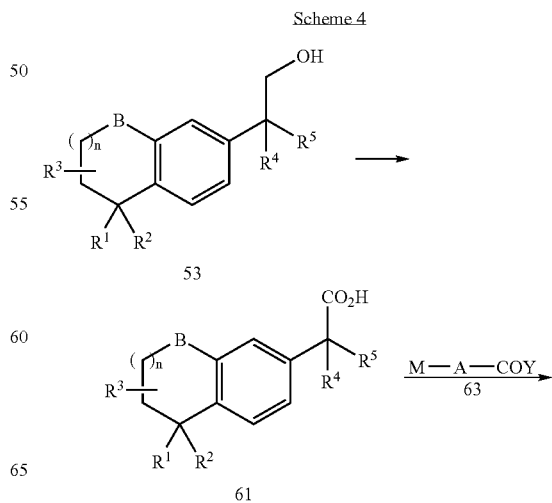

-continued

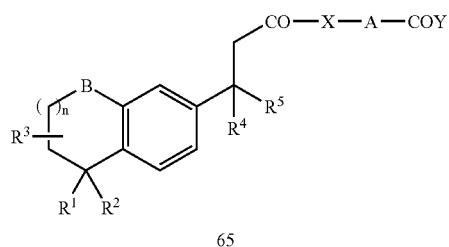

65

Scheme 5 illustrates conversion of alcohol 53 (B=NR$^6$, S or O) to a compound of Formula (I), where the linking group Z is an alkyne (—C≡C—). As before, when B=NR$^6$ and R$^6$ is hydrogen the nitrogen atom is protected before commencing the above sequence of steps and deprotected after formation of the alkyne. Alcohol 53 is oxidized to aldehyde 55, which is reacted with the dibromophosphonium ylide 67 to provide dibromoalkene 69. Dibromoalkene is converted to an alkyne which is then coupled to aryl or heteroaryl halide 71 to yield the desired alkyne 73.

Scheme 5

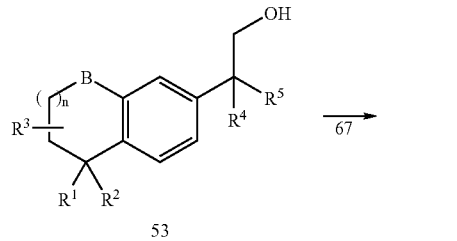

53

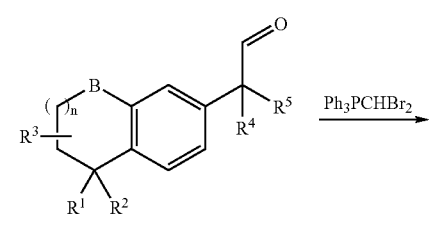

55

-continued

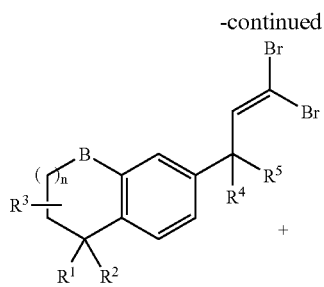

69

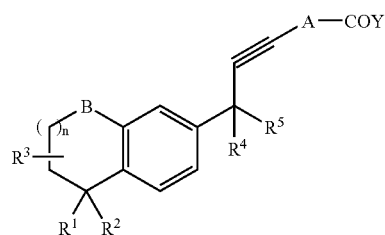

73

Scheme 6 illustrates conversion of alcohol 53 (B=NR$^6$, S or O) to a compound of Formula (I), where the linking group Z is an ether (—CH$_2$O—) or a thioether (—CH$_2$S—). As before, when B=NR$^6$ and R$^6$ is hydrogen the nitrogen atom is protected before commencing the above sequence of steps and deprotected after formation of the ether or thioether. Alcohol 53 is reacted with hydroxy derivative 75 under Mitsonobu conditions (e.g., triphenyl phosphine and diethyl azodicarboxylate) to directly provide ether 77. Alternatively, alcohol 53 may be converted to thiol 79 (e.g., thiourea, base, then hydrolysis) followed by reaction with hydroxy derivative 75 under Mitsunobu conditions to provide thioether 79.

Scheme 6

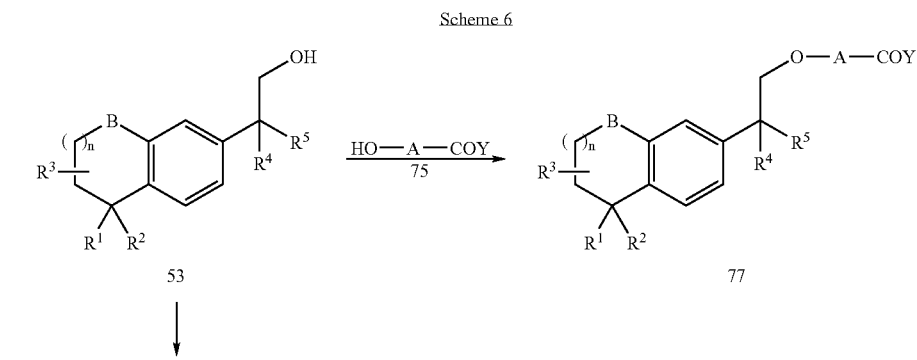

-continued

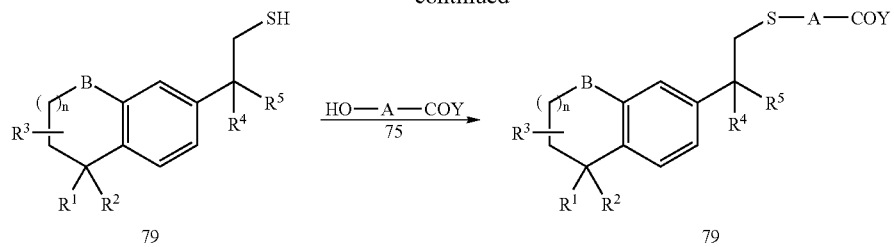

4.4. Assays

The retinoic acid receptor agonist selectivity of a compound of the invention may be determined by using ligand binding assays known to the skilled artisan (Apfel et al., Proc. Natl. Acad. Sci., 1992, 89, 7129; Teng et al., J. Med. Chem., 1997, 40, 2445; Bryce et al., U.S. Pat. No. 5,807,900 which are herein incorporated by reference). Treatment with RAR agonists, particularly RAR γ agonists may promote repair of alveolar matrix and septation, which are in important in treating emphysema. It should be noted that RAR agonists that are not γ selective may be effective in treating emphysema Transactivation, which is the ability of a retinoid to activate gene transcription when gene transcription is initiated by the binding of a ligand to the particular retinoic acid receptor being tested, may be determined by using methods described in the art (Apfel et al., Proc. Natl. Acad. Sci., 1992, 89, 7129; Bernard et al., Biochem. And Biophys. Res. Comm., 1992, 186, 977 which is herein incorporated by reference).

The suitability of the compounds of the invention in treating dermatological disorders caused by light or age and the promotion of wound healing may be determined by methods described in the art (Mustoe et al., Science 237, 1333 1987; Sprugel et al., J. Pathol., 129, 601, 1987, which are herein incorporated by reference). Methods described in the art may be used to determine the usefulness of the compounds of the invention to treating dermatological disorders such as acne or psoriasis (Boyd, Am. J. Med., 86, 568, 1989 and references therein; Doran et al., Methods in Enzynology, 190, 34, 1990, which are herein incorporated by reference). Finally, the ability of the compounds of the invention to treat cancer may also be determined by methods described in the art (Sporn et al., Fed. Proc. 1976, 1332; Hong et al., "Retinoids and Human Cancer" in The Retinoids: Biology, Chemistry and Medicine, M. B. Sporn, A. B. Roberts and D. S. Goodman (eds.) Raven Press, New York, 1994, 597-630, which are herein incorporated by reference).

4.5 Pharmaceutical Compositions and Modes of Administration

Compounds of the invention disclosed herein are useful for promoting the repair of damaged alveoli and septation of alveoli. Thus, methods of the invention may be employed to treat pulmonary diseases such as emphysema. The methods of treatment using a compound of the invention disclosed herein also may be used to treat cancer and dermatological disorders.

When used to treat or prevent emphysema or related diseases, cancer or dermatological disorders, compounds of the invention may be administered or applied singly or in combination with other agents. The compounds of the invention may also be administered or applied singly or in combination with other pharmaceutically active agents including other compounds of the invention. A compound of the invention can be administered or applied per se or as pharmaceutical compositions. The specific pharmaceutical formulation will depend upon the desired mode of administration, and will be apparent to those having skill in the art. Numerous compositions for the oral, topical or parental administration of retinoid agonists are known in the art. Any of these compositions may be used to formulate a compound of the invention.

Pharmaceutical compositions comprising a compound of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

For topical administration a compound of the invention may be formulated as solutions, gels, ointments, creams, suspensions, etc. as are well-known in the art.

Systemic formulations include those designed for administration by injection or infusion e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include but are not limited to sodium channel blockers, antibiotics, N-acetyl cysteine, homocysteine and phospholipids.

For injection, a compound of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Such compositions are preferably sterile.

Alternatively, compounds of the invention may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, a compound of the invention can be readily formulated by combination with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. Methods for formulating retinoid analogues for oral administration have been described in the art (See, e.g., the formulation of Accutane®, *Physicians' Desk Reference* 54$^{th}$ Ed., p. 2610, 2000).

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the compositions may take the form of tablets, lozenges, etc. formulated in conventional manner.

A compounds of the invention may also be administered directly to the lung by inhalation for the treatment of cancer, emphysema or dermatological disorders (see e.g., Tong et al., PCT Application, WO 97/39745; Clark et al., PCT Application, WO 99/47196, which are herein incorporated by reference). For administration by inhalation, a compound of the invention may be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas may be used to deliver compounds of the invention directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device may be used to administer a compound of the invention to the lung (See, e.g.,. Raleigh et al., *Proc. Amer. Assoc. Cancer Research Annual Meeting*, 1999, 40, 397, which is herein incorporated by reference). DPI devices typically use a mechanism such as a burst of gas to create a cloud of dry powder inside a container, which may then be inhaled by the patient. DPI devices are also well known in the art and may be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator may be formulated containing a powder mix of a compound of the invention and a suitable powder base such as lactose or starch for these systems.

Another type of device that may be used to deliver a compound of the invention to the lung is a liquid spray device supplied, for example, by Aradigm Corporation. Liquid spray systems use extremely small nozzle holes to aerosolize liquid drug formulations that may then be directly inhaled into the lung.

In one preferred embodiment, a nebulizer device is used to deliver a compound of the invention to the lung. Nebulizers create aerosols from liquid drug formulations by using, for example, ultrasonic energy to form fine particles that may be readily inhaled (see e.g., Verschoyle et al., *British J. Cancer*, 1999, 80, Suppl. 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In another preferred embodiment, an electrohydrodynamic ("EHD") aerosol device is used to deliver a compound of the invention to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of a compound of the invention formulation may be important parameters to optimize when delivering this compound to the lung with an EHD aerosol device and such optimization is routinely performed by one of skill in the art. EHD aerosol devices may more efficiently deliver drugs to the lung than existing pulmonary delivery technologies. Other methods of intra-pulmonary delivery of a compound of the invention will be known to the skilled artisan and are within the scope of the invention.

Liquid drug formulations suitable for use with nebulizers and liquid spray devices and EHD aerosol devices will typically include a compound of the invention with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611, which are herein incorporated by reference).

A compound of the invention may also be formulated in rectal or vaginal compositions such as suppositories or retention enemas, e.g., containing conventional suppository bases such as cocoa butter or other glycerides.

In addition to the formulations described previously, a compound of the invention may also be formulated as a depot preparation. Such long acting formulations may be administered by implantation (for example subcutaneously or intramuscularly) or by intramuscular injection. Thus, for example, a compound of the invention may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver a compound of the invention. Certain organic solvents such as dimethylsulfoxide also may be employed, although usually at the cost of greater toxicity. A compound of the invention may also be delivered in a controlled release system. In one embodiment, a pump may be used (Sefton, CRC Crit. Ref. Biomed. Eng., 1987, 14, 201; Buchwald et al., Surgery, 1980, 88, 507; Saudek et al., N. Engl. J. Med., 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem., 1983, 23, 61; see also Levy et al., Science 1985, 228, 190; During et al., Ann. Neurol., 1989, 25, 351; Howard et al., 1989, J. Neurosurg. 71, 105). In yet another embodiment, a controlled-release system can be placed in proximity of the target of a compound of the invention, e.g., the lung, thus requiring only a fraction of the systemic dose (see, e.g., Goodson, in Medical Applications of Controlled Release, supra, vol. 2, pp. 115 (1984)). Other controlled-release system may be used (see e.g.,.Langer, Science, 1990, 249, 1527).

When a compound of the invention is acidic, it may be included in any of the above-described formulations as the free acid, a pharmaceutically acceptable salt, a pro-drug, solvate or hydrate. Pharmaceutically acceptable salts substantially retain the activity of the free acid and may be prepared by reaction with bases. Pharmaceutically acceptable salts include any known suitable salts of retinoic acids known in the art for administration to mammals. Pharmaceutical salts tend to be more soluble in aqueous and other protic solvents than the corresponding free acid form. Similarly, a compound of the invention may be included in any of the above-described formulations as a solvate, hydrate or pro-drug. Preferred pro-drugs include hydrolyzable ester derivatives such as aromatic esters, benzyl esters and lower alkyl esters such as ethyl, cyclopentyl, etc. Other pro-drugs are known to those of skill in the pharmaceutical arts.

4.5 Methods of Use, Dosage and Doses

A compound of the invention, or compositions thereof, will generally be used in an amount effective to achieve the intended purpose. Of course, it is to be understood that the amount used will depend on the method of administration.

For use to treat or prevent chronic obstructive pulmonary disease such as emphysema, cancer or dermatological disorders, compounds of the invention or compositions thereof, are administered or applied in a therapeutically effective amount. Therapeutically effective amounts of compounds of the invention for systemic administration may be found in the detailed disclosure provided herein.

The pharmacokinetic profile of the compounds of the invention is predictable and can be described by using linear pharmacokinetic theory. Importantly, the pharmacokinetics of compounds of the invention in humans may be readily determined by one of skill in the art. The skilled artisan may determine a range of standard pharmacokinetic parameters after single oral dosing with a compound of the invention using procedures described in the art (see e.g., Khoo et al., J. Clin. Pharm, 1982, 22, 395; Colburn et al., J. Clin. Pharm, 1983, 23, 534; Colburn et al., Eur. J. Clin. Pharm., 1983, 23, 689). The skilled artisan may also measure values of these pharmacokinetic parameters after multiple dosing, following procedures described in the art, to determine whether induction or accumulation of the compound of the invention occurs under these circumstances (Brazzel et al., Eur. J. Clin. Pharm., 1983, 24, 695; Lucek et al., Clin. Pharmacokinetics, 1985, 10, 38). Those of skill in the art may estimate the appropriate systemic dosage levels of compounds of the invention necessary to treat emphysema, cancer or dermatological disorders in mammals (preferably, humans) using the pharmacokinetic parameters determined by the above procedures in conjunction with animal model dosage data.

Dosage amounts and intervals may be adjusted individually to provide plasma levels of a compound of the invention which are sufficient to maintain therapeutic effect. Usual patient dosages for administration by injection range from 0.1 µg and about 10.0 mg, preferably, between about 1.0 µg and about 1.0 mg, more preferably, between about 10.0 µg and about 300.0 µg, most preferably between about 50.0 µg and about 200 µg. Therapeutically effective serum levels may be achieved by administering a single daily dose or multiple doses each day.

The amount of a compound of the invention administered will, of course, be dependent on, among other factors, the subject being treated, the subject's weight, the severity of the affliction, the manner of administration and the judgment of the prescribing physician. For example, the dosage may be delivered in a pharmaceutical composition by a single administration, by multiple applications or controlled release. Dosing may be repeated intermittently, may be provided alone or in combination with other drugs and will continue as long as required for effective treatment of emphysema.

Preferably, a therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating emphysema, cancer or dermatological disorders when compared to other retinoid agonists. The dosage of a compound of the inventions described herein will preferably be within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (see, e.g., Fingl et al., 1975, In: The Pharmacological Basis of Therapeutics, Ch. 1, p.1). For example, a therapeutically effective dose of a compound of the invention may be administered either orally or directly into the lung.

5. EXAMPLES

The invention is further defined by reference to the following examples describing in detail the preparation of the compound and compositions of the invention. It will be apparent to those skilled in the art that many modifications, both to materials and methods, may be practiced without departing from the scope of the invention.

Example 5.1

Synthesis of (RAC)-4-[2-(4,4-DIMETHYL-CHROMAN-7-YL)-HEPTYLOXY]-BENZOIC ACID

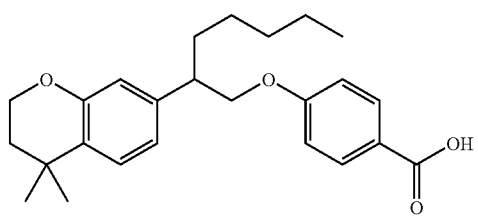

Step 1

A solution of 3-bromophenol (10.0 g, 57.8 mmole) in 50 mL of ethyl acrylate was treated with 0.9 mL of Triton B. The reaction mixture was heated at reflux for 18 hours. Excess ethyl acrylate was removed by distillation at atmospheric pressure. The resulting residue was diluted with 50 mL toluene and co-evaporated. The remaining product was diluted in 100 mL ether and washed with two 50 mL portions of sodium carbonate solution, 50 mL water and 50 mL saturated aqueous sodium chloride solution. The organic phase was dried over MgSO$_4$, filtered and concentrated in vacuo to give a pale yellow liquid. The product was purified by flash chromatography (SiO$_2$, 5% ethyl acetate in hexanes) to afford 6.435 g of 3-(3-bromo-phenoxy)-propionic acid ethyl ester as a colorless liquid.

Step 2

A solution of 3-(3-bromo-phenoxy)-propionic acid ethyl ester (6.435 g, 23.6 mmole) in 50 mL of anhydrous THF at 0° C. was treated dropwise with 23.6 mL of 3M methylmagnesium chloride solution in THF. The reaction mixture was kept at 0° C. for 30 minutes, allowed to warm to room temperature over 15 hours, carefully quenched by the addition of 100 mL saturated aqueous ammonium chloride solution and then extracted with three 50 mL portions of ether. The combined organic extracts were dried over MgSO$_4$, filtered and concentrated in vacuo to give a pale yellow oil. The product was purified by flash chromatography (SiO$_2$, 20% ethyl acetate in hexanes) to yield 5.741 g of 4-(3-bromo-phenoxy)-2-methyl-butan-2-ol as a translucent oil.

Step 3

A solution of 4-(3-bromo-phenoxy)-2-methyl-butan-2-ol (5.741 g, 22.2 mmole) in 45 mL of nitromethane was added dropwise to a suspension of aluminum chloride (4.019 g, 30.1 mmole) in 45 mL of nitromethane. The reaction mixture was stirred at room temperature for two hours and then poured onto 300 mL of ice-water. The pH was adjusted to 2.0 with 10% HCl and the product was extracted with three 100 mL portions of ether. The combined organic extracts were dried over MgSO$_4$, filtered and concentrated in vacuo to give a purple oil. The product was purified by flash chromatography (SiO$_2$, 1% ethyl acetate in hexanes) to yield 4.667 g of 7-bromo4,4-dimethyl-chroman as a colorless oil, which contained about 16% of 5-bromo-4,4-dimethyl-chroman.

Step 4

A solution of 7-bromo-4,4-dimethyl-chroman (1.0 g, 4.15 mmole) in 20 mL of THF at −78° C., was treated with 1.91 mL of 2.5M butyllithium. After 30 minutes at −78° C. a solution of hexanoic acid methoxy-methyl-amide (0.726 g, 4.56 mmole) in 5 mL of THF was added. The reaction mixture was stirred at −78° C. for 30 minutes, warmed to room temperature, quenched by the addition of 25 mL saturated aqueous ammonium chloride solution and extracted with three 25 mL portions of ether. The combined organic extracts were dried over MgSO$_4$, filtered and concentrated in vacuo to give a yellow oil. The product was purified by flash chromatography (SiO$_2$, 5% ethyl acetate in hexanes) to yield 0.516 g of 1-(4,4-dimethyl-chroman-7-yl)-hexan-1-one as a colorless oil.

Step 5

A suspension of methyl triphenylphosphonium bromide (1.062 g, 2.97 mmole) in 20 mL of THF at 0° C. was treated dropwise with 1.2 mL of a 2.5M butyllithium solution. The mixture was stirred at room temperature for 30 minutes and then cooled to 0° C. A solution of 1-(4,4-dimethyl-chroman-7-yl)-hexan-1-one (0.516 g, 1.98 mmole) in 5 mL of THF was added to the ylide solution. The reaction mixture was stirred at room temperature for one hour, quenched by the addition of 25 mL water and extracted with three 25 mL portions of ether. The combined organic extracts were dried over MgSO$_4$, filtered and concentrated in vacuo to give a yellow solid. The product was purified by flash chromatography (SiO$_2$, 2% ethyl acetate in hexanes) to yield 0.442 g of 4,4-dimethyl-7-(1-methylene-hexyl)-chroman as a colorless oil.

Step 6

A solution of 4,4-dimethyl-7-(1-methylene-hexyl)-chroman (0.442 g, 1.71 mmole) in 8 mL of THF at 0° C. was treated with 1.71 mL of 1M BH$_3$.THF complex. The reaction mixture was stirred at room temperature for three hours and then cooled to 0° C. The mixture was treated successively with 0.3 mL of water, 0.34 mL of 3M sodium hydroxide and 0.34 mL of 30% hydrogen peroxide, stirred at room temperature for two hours and then diluted with 10 mL of water. The pH was adjusted to 4.0 with 10% HCl and extracted with three 12.5 mL portions of ether. The combined-organic extracts were dried over MgSO$_4$, filtered and concentrated in vacuo to give a pale yellow oil. The product was purified by flash chromatography (SiO$_2$, 10-20% ethyl acetate in hexanes) to yield 0.366 g of 2-(4,4-dimethyl-chroman-7-yl)-heptan-1-ol as a colorless oil.

Step 7

A solution of 2-(4,4-dimethyl-chroman-7-yl)-heptan-1-ol (0.366 g, 1.32 mmole) in 27 mL of THF was treated with 0.222 g of methyl 4-hydroxybenzoate, 0.382 g of triphenylphosphine and 0.23 mL of diethyl azodicarboxylate (DEAD). The reaction mixture was heated at reflux for two hours, diluted with 50 mL of ether and then washed with two 25 mL portions of water and 25 mL of saturated aqueous sodium chloride solution. The organic phase was dried over MgSO$_4$, filtered and concentrated in vacuo to give a yellow oil. The product was purified by flash chromatography (SiO$_2$, 7% ethyl acetate in hexanes) to yield 0.474 g of 4-[2-(4,4-dimethyl-chroman-7-yl)-heptyloxy]-benzoic acid methyl ester, as a pale yellow oil.

Step 8

A solution of 4-[2-(4,4-dimethyl-chroman-7-yl)-heptyloxy]-benzoic acid methyl ester (0.474 g, 1.15 mmole) in 8 mL of ethanol was treated with a solution of potassium hydroxide (1.3 g) in 5 mL of water. THF (4 mL) was added and the mixture was heated at 45° C. for two hours, diluted with 20 mL of water and the pH was adjusted to 2 with concentrated HCl. The mixture was then extracted with three 20 mL portions of ethyl acetate. The combined organic extracts were dried over MgSO$_4$, filtered and concentrated in vacuo to give a pale yellow foam. The product was purified by recrystallization from acetonitrile/water to yield 0.362 g of 4-[2-(4,4-dimethyl-chroman-7-yl)-heptyloxy]-benzoic acid (1) as a white solid. M.p.: 91.5-93.3° C.

Example 5.2

Synthesis of (RAC)-4-[2-(4,4-DIMETHYL-THIO-CHROMAN-7-YL)-HEPTYLOXY]-BENZOIC ACID

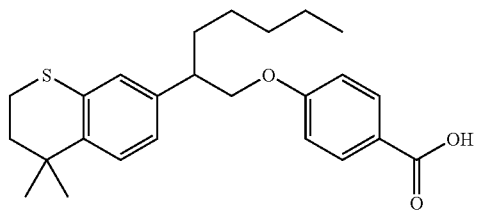

Step 1

A solution of 3-bromothiophenol (5.0 g) in 60 mL of DMF was treated with 3.75 g of ground potassium carbonate and 3.2 mL of 3,3-dimethylallyl bromide. The reaction mixture was stirred at room temperature for two hours, poured onto 75 mL of ice-water, acidified to pH 2.0 with 10% HCl and extracted with three 75 mL portions of ether. The organic phase was dried over MgSO$_4$, filtered and concentrated in vacuo to give a yellow oil. The product was purified by short path distillation (T=170° C. at 950 mTorr) to give 5.651 g of 1-bromo-3-(3-methyl-but-2-enylsulfanyl)-benzene as a colorless liquid.

Step 2

A solution of 1-bromo-3-(3-methyl-but-2-enylsulfanyl)-benzene (5.651 g, 22 mmole) in 100 mL of toluene was treated with 5.433 g of p-toluenesulfonic acid monohydrate and heated at reflux for 15 hours. The mixture was diluted with 100 mL of water, neutralized with solid sodium bicarbonate and extracted with two 100 mL portions of ethyl acetate. The organic phase was dried over MgSO$_4$, filtered and concentrated in vacuo to give a yellow oil. The product was purified by short path distillation (T=190° C. at 1.08 Torr) to give 4.902 g of 7-bromo-4,4-dimethyl-thiochroman as a pale yellow oil, which contained approximately 20% 5-bromo-4,4-dimethyl-thiochroman.

Step 3

A solution of 7-bromo-4,4-dimethyl-thiochroman (2.0 g, 7.78 mmole) in 45 mL of THF at −78° C. was, treated with 3.9 mL of 2.5M butyllithium. After 30 minutes at −78° C. a solution of hexanoic acid methoxy-methyl-amide (1.486 g, 9.33 mmole) in 5 mL of THF was added. The reaction mixture was stirred at −78° C. for 30 minutes, warmed to room temperature, quenched by the addition of 50 mL of saturated aqueous ammonium chloride solution and extracted with three 50 mL portions of ether. The combined organic extracts were dried over MgSO$_4$, filtered and concentrated in vacuo to give a yellow oil. The product was purified by flash chromatography (SiO$_2$, 3% ethyl acetate in hexanes) to yield 1.183 g of 1-(4,4-dimethyl-thiochroman-7-yl)-hexan-1-one as a pale yellow oil.

Step 4

A suspension of methyl triphenylphosphonium bromide (2.293 g, 6.42 mmole) in 40 mL of THF at 0° C., was treated dropwise with 2.6 mL of 2.5M butyllithium. The mixture was stirred at room temperature for 30 minutes and then cooled to 0° C. A solution of 1-(4,4-dimethyl-thiochroman-7-yl)-hexan-1-one (1.183 g, 4.28 mmole) in 10 mL of THF was added to the ylide solution. The reaction mixture was stirred at room temperature for one hour, quenched by the addition of 50 mL water and was extracted with three 50 mL portions of ether. The combined organic extracts were dried over MgSO$_4$, filtered and concentrated in vacuo to give a yellow solid. The product was purified by flash chromatography (SiO$_2$, 1% ethyl acetate in hexanes) to yield 0.939 g of 4,4-dimethyl-7-(1-methylene-hexyl)-thiochroman as a colorless oil.

Step 5

A solution of 4,4-dimethyl-7-(1-methylene-hexyl)-thiochroman (0.939 g, 3.42 mmole) in 15 mL of THF at 0° C., was treated with 3.42 mL of 1M BH$_3$.THF complex. The reaction mixture was stirred at room temperature for three hours and then cooled to 0° C. The mixture was treated successively with 0.59 mL of water, 0.67 mL of 3M sodium hydroxide and 0.67 mL of 30% hydrogen peroxide. The reaction mixture was stirred at room temperature for two hours and then diluted with 20 mL of water. The pH was adjusted to 4.0 with 10% HCl and then extracted with three 25 mL portions of ether. The combined organic extracts were dried over MgSO$_4$, filtered and concentrated in vacuo to give a pale yellow oil. The product was purified by flash chromatography (SiO$_2$, 10% ethyl acetate in hexanes) to yield 0.532 g of 2-(4,4-dimethyl-thiochroman-7-yl)-heptan-1-ol as a colorless oil.

Step 6

A solution of 2-(4,4-dimethyl-chroman-7-yl)-heptan-1-ol (0.532 g, 1.82 mmole) in 35 mL of THF was treated with 0.304 g of methyl 4-hydroxybenzoate, 0.525 g of triphenylphosphine and 0.32 mL of diethyl azodicarboxylate (DEAD). The reaction mixture was heated at reflux for two hours, diluted with 70 mL of ether and washed with two 35 mL portions of water and 35 mL of saturated aqueous sodium chloride solution. The organic phase was dried over MgSO$_4$, filtered and concentrated in vacuo to give a yellow oil. The product was purified by flash chromatography (SiO$_2$, 5% ethyl acetate in hexanes) to yield 0.715 g of 4-[2-(4,4-dimethyl-thiochroman-7-yl)-heptyloxyl-benzoic acid methyl ester as a pale yellow oil.

Step 7

A solution of 4-[2-(4,4-dimethyl-thiochroman-7-yl)-heptyloxy]-benzoic acid methyl ester (0.715 g, 1.68 mmole) in 12 mL of ethanol was treated with a solution of potassium hydroxide (1.9 g) in 7.5 mL of water. THF (5 mL) was added and the mixture was heated at 45° C. for two hours, diluted with 30 mL of water and the pH adjusted to 2.0 with concentrated HCl. The mixture was extracted with three portions of 30 mL of ethyl acetate. The organic phase was dried over MgSO$_4$, filtered and concentrated in vacuo to give a pale yellow foam. The product was purified by trituration in pentane, to yield 0.617 g of 4-[2-(4,4-dimethyl-thiochroman-7-yl)-heptyloxy]-benzoic acid as an off-white solid. M.p.: 123.0-123.5° C.

Example 5.3

Synthesis of (RAC) 4-[3-(4,4-DIMETHYL-CHROMAN-7-YL)-OCT-1-ENYL]-BENZOIC ACID

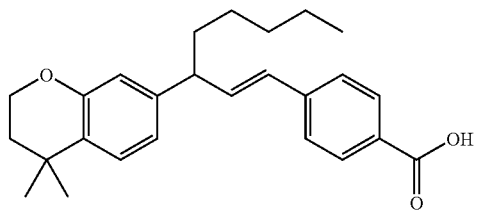

Step 1

To a solution of oxalyl chloride (0.15 mL) in 9 mL of dichloromethane at −78° C. was added 0.19 mL of DMSO. The mixture was stirred at −78° C. for 5 minutes and then a solution of 2-(4,4-dimethyl-chroman-7-yl)-heptan-1-ol (0.22 g, 0.79 mmole, from Example 1) in 3 mL of dichloromethane was added. The mixture was stirred at −78° C. for 15 minutes then 0.56 mL of triethylamine was added. Stirring was continued at −78° C. for another 15 minutes then at room temperature for two hours. The reaction mixture was quenched by the addition of 20 mL of water, extracted with three 20 mL portions of dichloromethane and the combined organic extracts were washed with two 20 mL portions of water and 20 mL of saturated aqueous sodium chloride solution. The organic phase was dried over MgSO$_4$, filtered and concentrated in vacuo to give a yellow oil. The product was purified by flash chromatography (SiO$_2$, 10% ethyl acetate in hexanes) to afford 0.16 g of 2-(4,4-dimethyl-chroman-7-yl)-heptanal as a colorless oil.

Step 2

A solution of 4-(diethoxyphosphorylmethyl)-benzoic acid methyl ester (0.25 g, 0.87 mmole) in 5 mL of THF at −20° C., was treated with 0.88 mL of 1M lithium bis(trimethylsilyl)amide solution in hexanes. The mixture was stirred at −20° C. for 20 minutes before a solution of 2-(4,4-dimethyl-chroman-7-yl)-heptanal (0.16 g, 0.58 mmole) in 5 mL of THF was added. The reaction mixture was stirred at −20° C. for 30 minutes, at room temperature for 6 hours, quenched by the addition of 10 mL of saturated aqueous ammonium chloride solution and extracted with three 10 mL portions of ethyl acetate. The combined organic extracts were dried over MgSO$_4$, filtered and concentrated in vacuo, to give a yellow oil. The product was purified by flash chromatography (SiO$_2$, 10% ethyl acetate in hexanes) to yield 0.1 g of 4-[3-(4,4-dimethyl-chroman-7-yl)-oct-1-enyl]-benzoic acid methyl ester as a colorless oil.

Step 3

A solution of 4-[3-(4,4-dimethyl-chroman-7-yl)-oct-1-enyl]-benzoic acid methyl ester (0.1 g, 0.25 mmole) in 25 mL of a 4:1 THF/methanol mixture was treated with a solution of 0.1 g of lithium hydroxide monohydrate in 5 mL of water. The reaction mixture was stirred at 40° C. for 2 hours, concentrated in vacuo and the pH adjusted to 3-4 with 1N HCl solution. The mixture was extracted with three 25 mL portions of ethyl acetate. The combined organic extracts were dried over MgSO$_4$, filtered and concentrated in vacuo to give 0.06 g of 4-[3-(4,4-dimethyl-chroman-7-yl)-oct-1-enyl]-benzoic acid as a colorless glassy oil. MS (EI): (M$^-$−1): 391.

Example 5.4

Synthesis of (RAC) 4-[3-(4,4-DIMETHYL-THIOCHROMAN-7-YL)-OCT-1-ENYL]-BENZOIC ACID

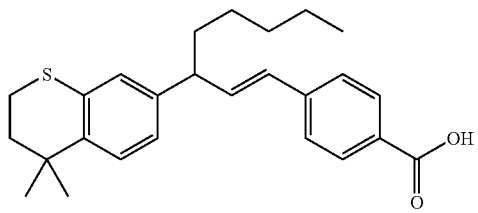

Following the procedure described in Example 3, but substituting 2-(4,4-dimethyl-thiochroman-7-yl)-heptan-1-ol (from example 2) for 2-(4,4-dimethyl-chroman-7-yl)-heptan-1-ol in step 1, afforded 4-[3-(4,4-dimethyl-thiochroman-7-yl)-oct-1-enyl]-benzoic acid as a colorless glassy oil. MS (EI): (M$^-$−1): 407.

Example 5.5

Synthesis of (RAC)-4-[3-(1,4,4-TRIMETHYL-1,2,3,4-TETRAHYDRO-QUINOLIN-7-YL)-OCT-1-ENYL]-BENZOIC ACID

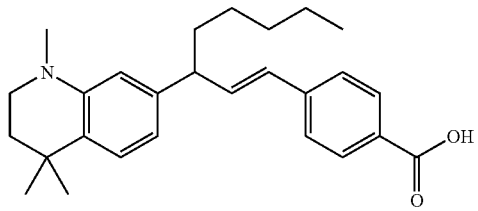

Step 1

A solution of 3-nitrophenyl acetic acid (12.755 g, 70.4 mmole) in 150 mL of ethanol was treated with 3.83 mL of concentrated sulfuric acid. The reaction mixture was heated at reflux for 20 hours, concentrated in vacuo to ⅓ the initial volume and diluted with 250 mL of ethyl acetate. The organic solution was, successively washed with two 100 mL portions of water, two 100 mL portions of saturated aqueous sodium bicarbonate solution, 100 mL of water and 100 mL of saturated aqueous sodium chloride solution. The organic phase was dried over MgSO$_4$, filtered and concentrated in vacuo to give 14.69 g of ethyl 3-nitrophenyl acetate as a pale yellow oil.

Step 2

A solution of ethyl 3-nitrophenyl acetate (4.0 g, 19.1 mmole) in 80 mL of DMF was treated with 12.46 g of cesium carbonate and 2.55 mL of pentyl iodide. The reaction mixture was stirred at room temperature for 15 hours, diluted with 200 mL of water and extracted with three portions of 150 mL of ether. The combined organic extracts were washed with 200 mL water and 200 mL of saturated aqueous sodium chloride solution. The organic phase was dried over MgSO$_4$, filtered and concentrated in vacuo to give a yellow oil. The product was purified by flash chromatography ($SiO_2$, 5% ethyl acetate in hexanes) to yield 4.451 g of 2-(3-nitro-phenyl)-heptanoic acid ethyl ester as a pale yellow oil.

Step 3

A solution of 2-(3-nitro-phenyl)-heptanoic acid ethyl ester (4.451 g, 15.9 mmole) in 150 mL of ethyl acetate containing 1.69 g of 10% palladium on carbon was subjected to atmospheric pressure of hydrogen for 15 hours. The mixture was filtered through a Celite/$SiO_2$ pad and the volatiles were removed in vacuo to yield 3.866 g of 2-(3-amino-phenyl)-heptanoic acid ethyl ester as a pale yellow oil.

Step 4

A solution of 2-(3-amino-phenyl)-heptanoic acid ethyl ester (3.866 g, 15.5 mmole) in 40 mL of chloroform was treated with 1.73 mL of 3,3-dimethylacryloyl chloride. The mixture was heated at reflux for four hours, quenched by the addition of 100 mL water and extracted with three 50 mL portions of chloroform. The combined organic extracts were washed with 100 mL of saturated aqueous sodium bicarbonate solution, 100 mL of water and 100 mL of saturated aqueous sodium chloride solution. The organic phase was dried over $MgSO_4$, filtered and concentrated in vacuo to give a yellow oil. The product was purified by flash chromatography ($SiO_2$, 15% ethyl acetate in hexanes) to yield 3.822 g of 2-[3-(3-methyl-but-2-enoylamino)-phenyl]-heptanoic acid ethyl ester as a pale yellow oil.

Step 5

A solution of 2-[3-(3-methyl-but-2-enoylamino)-phenyl]-heptanoic acid ethyl ester (3.822 g, 11.5 mmole) in 60 mL of dichloromethane was treated with 4.613 g of aluminum chloride and heated at reflux for four hours. The reaction mixture was poured onto 200 mL of ice-water and extracted with two 100 mL portions of dichloromethane. The combined organic extracts were washed with 200 mL of saturated aqueous sodium bicarbonate solution. The organic phase was dried over $MgSO_4$, filtered and concentrated in vacuo to give a yellow oil. The product was purified by flash chromatography ($SiO_2$, 25% ethyl acetate in hexanes) to yield 3.657 g of 2-(4,4-dimethyl-2-oxo-1,2,3,4-tetrahydro-quinolin-7-yl)-heptanoic acid ethyl ester as a pale yellow oil.

Step 6

A solution of 2-(4,4-dimethyl-2-oxo-1,2,3,4-tetrahydro-quinolin-7-yl)-heptanoic acid ethyl ester (3.657 g, 11 mmole) in 100 mL of ether was treated with 1.6 g of lithium aluminum hydride, heated at reflux for four hours and then cooled to 0° C. The reaction mixture was quenched by the successive addition of 1.6 mL water, 1.6 mL 15% sodium hydroxide solution and 4.8 mL water and stirred at room temperature until a white precipitate formed. $MgSO_4$ was added and the mixture was filtered and concentrated in vacuo affording a yellow oil. The product was purified by flash chromatography ($SiO_2$, 25% ethyl acetate in hexanes) to yield 2.1 g of 2-(4,4-dimethyl-1,2,3,4-tetrahydro-quinolin-7-yl)-heptan-1-ol as a pale yellow oil.

Step 7

A solution of 2-(4,4-dimethyl-1,2,3,4-tetrahydro-quinolin-7-yl)-heptan-1-ol (2.1 g, 7.62 mmole) in 30 mL of THF was treated with 32 mL of a 1M sodium bis(trimethylsilyl) amide solution in THF. The reaction mixture was stirred at room temperature for 30 minutes and then a solution of 3.5 g of di-t-butyl dicarbonate in 30 mL of THF was added. The mixture was stirred at room temperature for 15 hours, quenched by the addition of 100 mL saturated aqueous ammonium chloride solution and extracted with three 100 mL portions of ether. The combined organic phases were dried over $MgSO_4$, filtered and concentrated in vacuo to give an orange oil. The residue was taken up in 100 mL of methanol and treated with 10 mL of 1% potassium carbonate aqueous solution. The mixture was stirred at room temperature for two hours, concentrated in vacuo and the residue diluted with 200 mL of ether. The organic solution was washed with two 100 mL portions of water and 100 mL of saturated aqueous sodium chloride solution. The organic phase was dried over $MgSO_4$, filtered and concentrated in vacuo to give a dark yellow oil. The product was purified by flash chromatography ($SiO_2$, 10% ethyl acetate in hexanes) to yield 0.757 g of 7-(1-hydroxymethyl-hexyl)-4,4-dimethyl-3,4-dihydro-2H-quinoline-1-carboxylic acid tert-butyl ester as a yellow oil.

Step 8

A solution of 7-(1-hydroxymethyl-hexyl)-4,4-dimethyl-3,4-dihydro-2H-quinoline-1-carboxylic acid tert-butyl ester (1.27 g, 3.38 mmole) in 10 mL of dichloromethane was added to a suspension of 1.1 g of pyridinium chlorochromate in 15 mL of dichloromethane. The reaction mixture was stirred at room temperature for 6 hours, diluted with 50 mL of ether and filtered through a pad of Celite. The volatiles were removed in vacuo to give a brown oil. The product was purified by flash chromatography ($SiO_2$, 5% ethyl acetate in hexanes) to yield 0.91 g of 7-(1-formyl-hexyl)-4,4-dimethyl-3,4-dihydro-2H-quinoline-1-carboxylic acid tert-butyl ester as a yellow oil.

Step 9

A solution of 4-(dimethoxyphosphorylmethyl)-benzoic acid methyl ester (0.94 g, 3.6 mmole) in 10 mL of THF at −20° C., was treated with 3.7 mL of 1M lithium bis(trimethylsilyl)amide solution in hexanes. After 20 minutes at −20° C. a solution of 7-(1-formyl-hexyl)-4,4-dimethyl-3,4-dihydro-2H-quinoline-1-carboxylic acid tert-butyl ester (0.91 g, 2.4 mmole) in 5 mL of THF was added. The reaction mixture was stirred at −20° C. for 30 minutes, at room temperature for 6 hours, quenched by the addition of 10 mL of saturated aqueous ammonium chloride solution and extracted with three 10 mL portions of ethyl acetate. The combined organic extracts were dried over $MgSO_4$, filtered and concentrated in vacuo to give a yellow oil. The product was purified by flash chromatography ($SiO_2$, 5% ethyl acetate in hexanes) to yield 0.98 g of 7-{1-[2-(4-methoxy-carbonyl-phenyl)-vinyl]-hexyl}-4,4-dimethyl-3,4-dihydro-2H-quinoline-1-carboxylic acid tert-butyl ester as a pale yellow oil.

Step 10

A solution of 7-{1-[2-(4-methoxycarbonyl-phenyl)-vinyl]-hexyl}-4,4-dimethyl-3,4-dihydro-2H-quinoline-1-carboxylic acid tert-butyl ester (0.98 g) in 10 mL of dichloromethane was treated with 1.5 mL of trifluoroacetic acid. The mixture was stirred at room temperature for four hours and then was concentrated in vacuo to yield 0.72 g of 4-[3-(4,4-dimethyl-1,2,3,4-tetrahydro-quinolin-7-yl)-oct-1-enyl]-benzoic acid methyl ester as a yellow oil.

Step 11

A solution of 4-[3-(4,4-dimethyl-1,2,3,4-tetrahydro-quinolin-7-yl)-oct-1-enyl]-benzoic acid methyl ester (0.36 g, 0.88 mmole) in 10 mL of THF was cooled to −78° C. and was treated with 1.1 mL of a 1M lithium bis(trimethylsilyl) amide solution in hexanes. After 30 minutes at −78° C., 0.06 mL of methyl iodide was added. The mixture was stirred at room temperature for 7 hours, quenched by the addition of 10 mL of saturated aqueous ammonium chloride solution and extracted with two 10 mL portions of ethyl acetate. The combined organic extracts were dried over MgSO₄, filtered and concentrated in vacuo to give a yellow oil. The product was purified by flash chromatography (SiO₂, 5% ethyl acetate in hexanes) to yield 0.23 g of 4-[3-(1,4,4-trimethyl-1,2,3,4-tetrahydro-quinolin-7-yl)-oct-1-enyl]-benzoic acid methyl ester as a pale yellow oil.

Step 12

A solution of 4-[3-(1,4,4-trimethyl-1,2,3,4-tetrahydro-quinolin-7-yl)-oct-1-enyl]-benzoic acid methyl ester (0.23 g, 0.5 mmole) in 10 mL of a 1:1 THF/methanol mixture was treated with a solution of 0.09 g of lithium hydroxide monohydrate in 2.5 mL of water and stirred at 40° C. for 6 hours. The mixture was diluted with 10 mL of water and the pH adjusted to 2.0 with 2N HCl solution. The mixture was extracted with three 10 mL portions of ethyl acetate. The combined organic extracts were dried over MgSO₄, filtered and concentrated in vacuo to give a yellow oil. The product was purified by preparative tlc (SiO₂, 25% ethyl acetate in hexanes) to yield 0.095 g of 4-[3-(1,4,4-trimethyl-1,2,3,4-tetrahydro-quinolin-7-yl)-oct-1-enyl]-benzoic acid as a pale yellow oil. MS (EI): (M⁺): 405.

Example 5.6

Synthesis of (RAC)-4-[3-(1-ETHYL-4,4-DIMETHYL-1,2,3,4-TETRAHYDRO-QUINOLIN-7-YL)-OCT-1-ENYL]-BENZOIC ACID

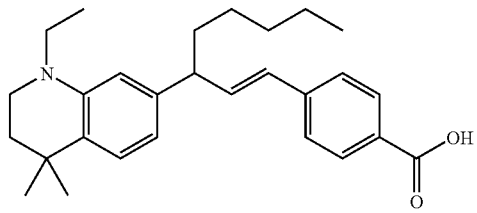

Following the procedure described in Example 5.5, but substituting ethyl iodide for methyl iodide in step 11, afforded 4-[3-(1-ethyl4,4-dimethyl-1,2,3,4-tetrahydro-quinolin-7-yl)-oct-1-enyl]-benzoic acid as a pale yellow oil. MS (EI): (M⁺+1): 421.

Example 5.7

Synthesis of (RAC)-4-[3-(1,4,4-TRIMETHYL-1,2,3,4-TETRAHYDRO-QUINOLIN-7-YL)-PENT-1-ENYL]-BENZOIC ACID

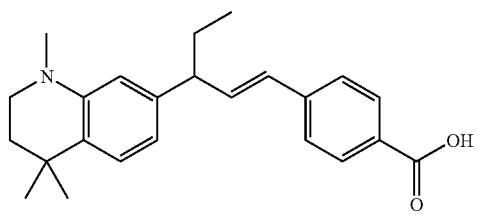

Following the procedure described in Example 5.5, but substituting ethyl iodide for pentyl iodide in step 2, afforded 4-[3-(1,4,4-trimethyl-1,2,3,4-tetrahydro-quinolin-7-yl)-pent-1-enyl]-benzoic acid as a pale yellow oil.

Example 5.8

Synthesis of (RAC)-4-[3-(1,4,4-TRIMETHYL-1,2,3,4-TETRAHYDRO-QUINOLIN-7-YL)-UNDEC-1-ENYL]-BENZOIC ACID

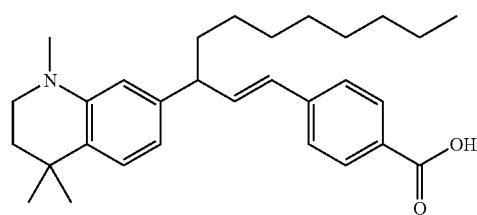

Following the procedure described in Example 5, but substituting octyl iodide for pentyl iodide in step 2, affords 4-[3-(1,4,4-trimethyl-1,2,3,4-tetrahydro-quinolin-7-yl)-undec-1-enyl]-benzoic acid as a pale yellow oil.

Example 5.9

Synthesis of (RAC)-4-[4-PHENYL-3-(1,4,4-TRIMETHYL-1,2,3,4-TETRAHYDRO-QUINOLIN-7-YL)-BUT-1-ENYL]-BENZOIC

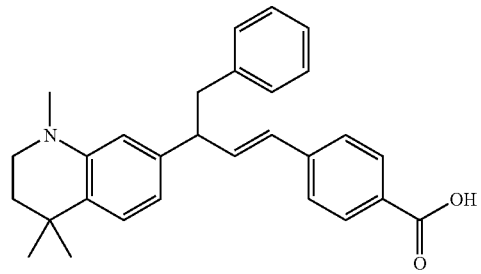

Following the procedure described in Example 5.5, but substituting benzyl bromide for pentyl iodide in step 2, affords 4-[4-phenyl-3-(1,4,4-trimethyl-1,2,3,4-tetrahydro-quinolin-7-yl)-but-1-enyl]-benzoic acid as a pale yellow oil.

Example 5.10

Synthesis of (RAC)-4-[3-(4,4-DIMETHYL-1,2,3,4-TETRAHYDRO-QUINOLIN-7-YL)-OCT-1-ENYL]-BENZOIC ACID

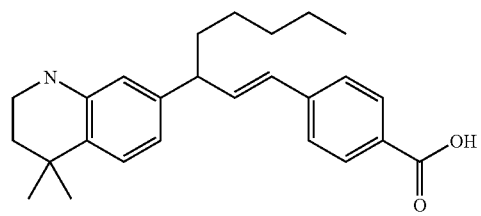

Following the procedure described in Example 5.5, but eliminating step 11 (no N-alkylation) afforded 4-[3-(4,4-dimethyl-1,2,3,4-tetrahydro-quinolin-7-yl)-oct-1-enyl]-benzoic acid as a pale yellow oil. MS (ET) (M⁺+1): 392.

Example 5.11

Synthesis of (RAC)-3-FLUORO-4-[3-(1,4,4-TRIMETHYL-1,2,3,4-TETRAHYDRO-QUINOLIN-7-YL)-OCT-1-ENYL]-BENZOIC

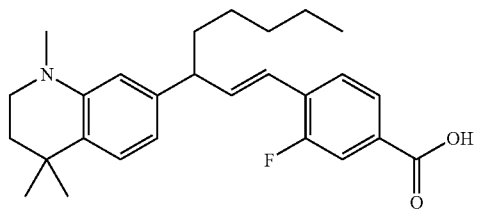

Following the procedure described in Example 5.5, but substituting 3-fluoro-4-(dimethoxyphosphorylmethyl)-benzoic acid methyl ester in step 9 for 4-(dimethoxyphosphorylmethyl)-benzoic acid methyl ester afforded 3-fluoro-4-[3-(1,4,4-trimethyl-1,2,3,4-tetrahydro-quinolin-7-yl)-oct-1-enyl]-benzoic acid as a pale yellow oil. MS (EI) ($M^+$+1): 423.

Example 5.12

Synthesis of (RAC)-4-[2-(1,4,4-TRIMETHYL-1,2,3,4-TETRAHYDRO-QUINOLIN-7-YL)-HEPTYLOXY]-BENZOIC ACID

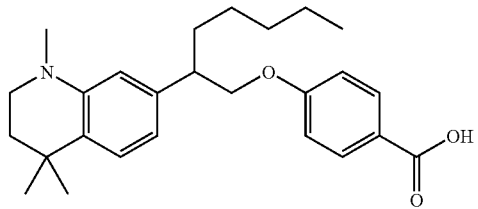

Step 1

A solution of 2-(4,4-dimethyl-1,2,3,4-tetrahydro-quinolin-7-yl)-heptan-1-ol (from Example 5.5, step 6) (2.52 g, 9.15 mmole) in 35 mL of acetonitrile was cooled to 0° C. and treated with 6.68 mL of a 37% formaldehyde solution, 5.82 g of sodium triacetoxyborohydride and 2.36 mL of acetic acid. The reaction mixture was stirred at 0° C. for 30 minutes then at room temperature for four hours, diluted with 50 mL of water and extracted with two 50 mL portions of ethyl acetate. The combined organic extracts were dried over $MgSO_4$, filtered and concentrated in vacuo to give a yellow oil. The product was purified by flash chromatography ($SiO_2$, 25% ethyl acetate in hexanes) to yield 2.39 g of 2-(1,4,4-trimethyl-1,2,3,4-tetrahydro-quinolin-7-yl)-heptan-1-ol as a pale yellow oil.

Step 2

A solution of 2-(1,4,4-trimethyl-1,2,3,4-tetrahydro-quinolin-7-yl)-heptan-1-ol (1.2 g, 4.15 mmole) in 20 mL of THF was treated with 0.69 g of methyl 4-hydroxybenzoate, 1.2 g of triphenylphosphine and 0.72 mL of diethyl azodicarboxylate (DEAD) and heated at reflux for 6 hours. The mixture was diluted with 100 mL of ethyl acetate and washed with two 50 mL portions of water and 50 mL of saturated aqueous sodium chloride solution. The organic phase was dried over $MgSO_4$, filtered and concentrated in vacuo to give a yellow oil. The product was purified by flash chromatography ($SiO_2$, 10% ethyl acetate in hexanes) to yield 1.1 g of 4-[2-(1,4,4-trimethyl-1,2,3,4-tetrahydro-quinolin-7-yl)-heptyloxy]-benzoic acid methyl ester, as a pale yellow oil.

Step 3

A solution of 4-[2-(1,4,4-trimethyl-1,2,3,4-tetrahydro-quinolin-7-yl)-heptyloxy]-benzoic acid methyl ester (1.1 g, 2.6 mmole) in 14 mL of a 1:1 THF/methanol mixture was treated with a solution of 0.44 g of lithium hydroxide monohydrate in 5 mL of water and stirred at 40° C. for 6 hours. The mixture was diluted with 20 mL of water and the pH was adjusted to 2.0 with 2N HCl solution. The mixture was extracted with three 20 mL portions of ethyl acetate. The combined organic extracts were dried over $MgSO_4$, filtered and concentrated in vacuo to give a yellow oil. The product was purified by preparative tlc ($SiO_2$, 25% ethyl acetate in hexanes) to yield 0.875 g of 4-[2-(1,4,4-trimethyl-1,2,3,4-tetrahydro-quinolin-7-yl)-heptyloxy]-benzoic acid as a pale yellow oil. MS (EI): ($M^+$+1): 410.

Example 5.13

Synthesis of (RAC)-4-[2-(1-ETHYL-4,4-DIMETHYL-1,2,3,4-TETRAHYDRO-QUINOLIN-7-YL)-HEPTYLOXY]-BENZOIC ACID

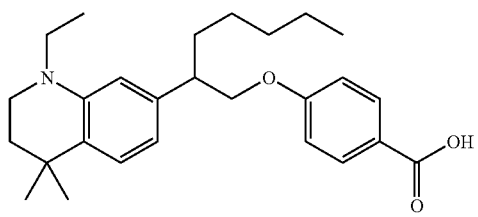

Following the procedure described in Example 5.12, but substituting acetaldehyde for formaldehyde in step 1, afforded 4-[2-(1-ethyl4,4-dimethyl-1,2,3,4-tetrahydro-quinolin-7-yl)-heptyloxy]-benzoic acid as a pale yellow oil. MS (EI): ($M^+$+1): 424.

Example 5.14

Synthesis of 4-[2-(4,4-DIMETHYL-CHROMAN-7-YL)-HEPTANOYLOXY]-BENZOIC ACID

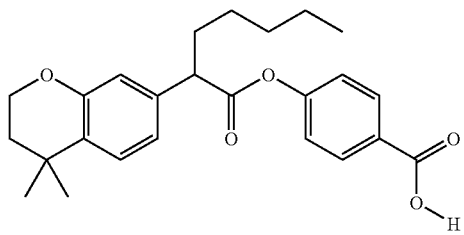

Step 1

A solution of 2-(4,4-dimethyl-chroman-7-yl)-heptan-1-ol (0.2 g, 0.72 mmol, from Example 5.1, Step 6) in 1.5 mL of CCL$_4$ and 2.2 mL of water containing 4 mg RuCl$_3$ was treated with 628 mg, 2.94 mmol of NaIO$_4$. The mixture was stirred at room temperature for 2.5 h, diluted with 10 mL of water and the pH adjusted to 2 with 10% aqueous HCl. The mixture was extracted with dichloromethane, concentrated to dryness, and purified via flash chromatography (0-20% ethyl acetate/hexane gradient elution) to give 105 mg (50%) of 2-(4,4-dimethyl-chroman-7-yl)-heptanoic acid.

Step 2

A solution of 2-(4,4-dimethyl-chroman-7-yl)-heptanoic acid (105 mg, 0.36 mmol) in 5 mL of dichloromethane with 91.6 mg, 0.4 mmol of benzyl 4-hydroxybenzoate and 44 mg, 0.36 mmol of DMAP was cooled to 0° C. and treated with 83 mg, 0.4 mmol of DCC. The mixture was kept at 0° C. for 15 minutes, then warmed to room temperature. After 2 h, the mixture was filtered and the resulting solution was washed with water and brine. The solution was dried and concentrated, then purified by flash chromatography (8% ethyl acetate/hexane) to give 152 mg (84%) of 4-[2-(4,4-dimethyl-chroman-7-yl)-heptanoyloxy]-benzoic acid benzyl ester.

Step 3

A solution of 4-[2-(4,4-dimethyl-chroman-7-yl)-heptanoyloxy]-benzoic acid benzyl ester (152 mg, 0.3 mmol) in 10 mL of elthyl acetate with 32 mg of 10% palladium on carbon, was subjected to 1 atm. H$_2$. After 2 h, the mixture was filtered through Celite and silica gel, concentrated under vacumn and purified by flash chromatography (gradient elution, 10-50% ethyl acetate/hexane) to afford 74 mg (59%) of 4-[2-(4,4-dimethyl-chroman-7-yl)-heptanoyloxy]-benzoic acid.

Example 5.15

Synthesis of 4-[2-(4,4-DIMETHYL-CHROMAN-7-YL)-HEPTANOYLAMINO]-BENZOIC ACID

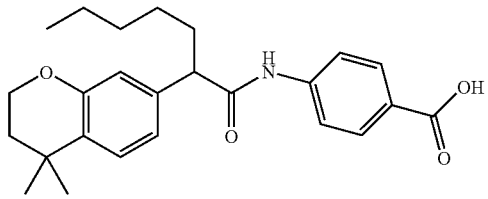

Step 1

To a solution of 2-(4,4-dimethyl-chroman-7-yl)-heptan-1-ol (0.27 g, 0.98 mmole, from Example 1, step 6) in a mixture of 2 mL of carbon tetrachloride, 2 mL acetonitrile and 3 mL water, containing 3-5 mg of ruthenium chloride, was added 0.85 g of sodium periodate. The mixture was stirred at room temperature for 2 hours, diluted with 10 mL of water, and pH was adjusted to 2 with 10% hydrochloric acid. The mixture was extracted with three 10 mL portions of dichloromethane. The organic phase was dried over MgSO$_4$, filtered and concentrated in vacuo to give a dark oil. The product was purified by flash chromatography (SiO$_2$, gradient from 0 to 20% ethyl acetate in hexanes) to yield 0.16 g of 2-(4,4-dimethyl-chroman-7-yl)-heptanoic acid as a pale yellow oil.

Step 2

A solution of 2-(4,4-dimethyl-chroman-7-yl)-heptanoic acid (0.16 g, 0.55 mmole) in 8 mL of dichloromethane was treated with 1 mL of oxalyl chloride and 0.06 mL of DMF. The reaction mixture was stirred at room temperature for 2 hours and concentrated in vacuo. The residue was dissolved in 5 mL of pyridine, and 0.17 g of methyl 4-aminobenzoate was added. The reaction mixture was stirred at 40° C. for 18 hours, diluted with 10 mL of water and extracted with three 10 mL portions of ethyl acetate. Combined extracts were washed with 10 mL of 1N hydrochloric acid, 10 mL of water and 10 mL of brine. The organic phase was dried over MgSO$_4$, filtered and concentrated in vacuo to give an oil. The product was purified by flash chromatography (SiO$_2$, 20% ethyl acetate in hexanes) to yield 0.15 g of 4-[2-(4,4-dimethyl-chroman-7-yl)-heptanoylamino]-benzoic acid methyl ester as a white foam.

Step 3

A solution of 4-[2-(4,4-dimethyl-chroman-7-yl)-heptanoylamino]-benzoic acid methyl ester (0.15 g, 0.35 mmole) in 10 mL of a 4:1 THF/methanol mixture was treated with a solution of 0.1 g of lithium hydroxide monohydrate in 2.5 mL of water and stirred at 40° C. for 6 hours. The mixture was diluted with 10 mL of water and the pH adjusted to 2.0 with 2N HCl solution. The mixture was extracted with three 10 mL portions of ethyl acetate. The combined organic extracts were dried over MgSO$_4$, filtered and concentrated in vacuo to give a yellow oil. The product was purified by flash chromatography (SiO$_2$, 10% methanol in dichloromethane) to yield 0.11 g of 4-[2-(4,4-dimethyl-chroman-7-yl)-heptanoylamino]-benzoic acid as a white powder. MS (ESI): (M$^-$): 408.

Example 5.16

Synthesis of 4-[3-(4,4-DIMETHYL-1,3,3,4-TETRAHYDRO-QUNOLIN-7-YL)-OCT-1-YNYL]-BENZOIC ACID

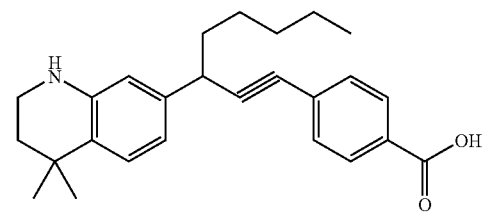

Step 1

To a solution of carbon tetrabromide (0.32 g, 0.96 mmole) in 5 mL of dichloromethane, at −20° C., was added triphenyl phosphine in 5 mL of dichloromethane. After stirring at 0° C. for 15 minutes reaction mixture was treated with a solution of 7-(1-formyl-hexyl)-4,4-dimethyl-3,4-dihydro-2H-quinoline-1-carboxylic acid tert-butyl ester (0.18 g, 0.48 mmole, from Example 5 step 8) in 2 mL of dichloromethane. The reaction mixture was stirred at room temperature for 4 hours, quenched by the successive addition of 5 mL of water and 1.5 mL of saturated sodium bicarbonate. The phases were separated and aqueous phase was extracted with two 25 mL portions of dichloromethane. Organic phase was dried over MgSO$_4$, filtered and concentrated in vacuo affording a brownish thick oil. The product was purified by flash chromatography (SiO$_2$, 20% ethyl acetate in hexanes) to yield 0.08 g of 7-(3,3-dibromo-1-pentyl-allyl)-4,4-dimethyl-3,4-dihydro-2H-quinoline-1-carboxylic acid tert-butyl ester as a colourless oil.

Step 2

A solution of 7-(3,3-dibromo-1-pentyl-allyl)-4,4-dimethyl-3,4-dihydro-2H-quinoline-1-carboxylic acid tert-butyl ester (0.08 g, 0.15 mmole) in 2 mL of THF at −78° C. was treated with 0.13 mL of 2.5M butyllithium. The reaction mixture was stirred at −78° C. for 1 hour, then at room temperature for 2 hours, quenched by the successive addition of 5 mL water and 5 mL of saturated aqueous ammonium chloride solution and extracted with three 25 mL portions of ether. The combined organic extracts were dried over MgSO$_4$, filtered and concentrated in vacuo to give a yellow oil. The product was purified by flash chromatography (SiO$_2$, 5% ethyl acetate in hexanes) to yield 0.049 g of 4,4-dimethyl-7-(1-pentyl-prop-2-ynyl)-3,4-dihydro-2H-quinoline-1-carboxylic acid tert-butyl ester as a colourless oil.

Step 3

A mixture of 0.043 g of methyl 4-iodobenzoate, 0.093 mL of triethylamine, 4.6 mg of Pd(Ph$_3$P)$_2$Cl$_2$ and 2.5 mg of copper (I) iodide in 2 ml of DMF was degassed and treated with a solution of 4,4-dimethyl-7-(1-pentyl-prop-2-ynyl)-3,4-dihydro-2H-quinoline-1-carboxylic acid tert-butyl ester (0.049 g, 0.13 mmole) in 1 mL of DMF. The reaction mixture was stirred at room temperature for 18 hours, diluted with 10 mL of water and extracted with-three 10 mL portions of ethyl acetate. The combined organic extracts were washed with 10 mL of 1N HCl, 10 mL of water and 10 ml of brine, dried over MgSO$_4$, filtered and concentrated in vacuo to give a yellow oil. The product was purified by flash chromatography (SiO$_2$, 10% ethyl acetate in hexanes) to yield 0.035 g of 7-[3-(4-methoxycarbonyl-phenyl)-1-pentyl-prop-2-ynyl]-4,4-dimethyl-3,4-dihydro-2H-quinoline-1-carboxylic acid tert-butyl ester.

Step 4

A solution of 7-[3-(4-methoxycarbonyl-phenyl)-1-pentyl-prop-2-ynyl]-4,4-dimethyl-3,4-dihydro-2H-quinoline-1-carboxylic acid tert-butyl ester (0.035 g, 0.07 mmole) in 5 mL of a 4:1 THF/methanol mixture was treated with a solution of 0.1 g of lithium hydroxide monohydrate in 2 mL of water and stirred at 40° C. for 2 hours. The mixture was diluted with 5 mL of water and the pH adjusted to 2 with 2N HCl solution. The mixture was extracted with three 10 mL portions of ethyl acetate. The combined organic extracts were dried over MgSO$_4$, filtered and concentrated in vacuo to give 0.03 g of 7-[3-(4-carboxy-phenyl)-1-pentyl-prop-2-ynyl]-4,4-dimethyl-3,4-dihydro-2H-quinoline-1-carboxylic acid tert-butyl ester as a yellow oil Step 5

A solution of 7-[3-(4-carboxy-phenyl)-1-pentyl-prop-2-ynyl]-4,4-dimethyl-3,4-dihydro-2H-quinoline-1-carboxylic acid tert-butyl ester (0.035 g, 0.07 mmole) in 2 mL of a 1:1 TFA/dichloromethane mixture was stirred for 30 minutes and concentrated. The residue was dissolved in 5 mL of dichloromethane and washed with 5 ml of saturated sodium bicarbonate, 5 mL of water and 5 mL of brine, the organic layer was dried over MgSO$_4$, filtered and concentrated in vacuo to give 0.02 g of 4-[3-(4,4-dimethyl-1,2,3,4-tetrahydro-quinolin-7-yl)-oct-1-ynyl]-benzoic acid as brownish oil. MS (ESI): (M$^-$): 388.

6. BIOLOGICAL ASSAYS

Example 6.1

Binding Affinity to and Transactivation of Retinoid Receptors

The retinoic acid receptor agonist selectivity of a compound of the invention may be determined by using ligand binding assays known to the skilled artisan (Apfel et al., *Proc. Natl. Acad. Sci.*, 1992, 89, 7129; Teng et al., *J. Med. Chem.*, 1997, 40, 2445; Bryce et al., U.S. Pat. No. 5,807,900 which are herein incorporated by reference). Treatment with RAR agonists, particularly RAR γ agonists may promote repair of alveolar matrix and septation, which are in important in treating emphysema It should be noted that RAR agonists that are not γ selective may be effective in treating emphysema.

Transactivation, which is the ability of a retinoid to activate gene transcription when gene transcription is initiated by the binding of a ligand to the particular retinoic acid receptor being tested, may be determined by using methods described in the art (Apfel et al., *Proc. Natl. Acad. Sci.*, 1992, 89, 7129; Bernard et al., *Biochem. And Biophys. Res. Comm.*, 1992, 186, 977 which is herein incorporated by reference).

Binding affinities of selected compounds of the invention are shown below.

| Example | Structure | Binding IC50 nM α/β/γ |
|---------|-----------|----------------------|
| 5.1 | 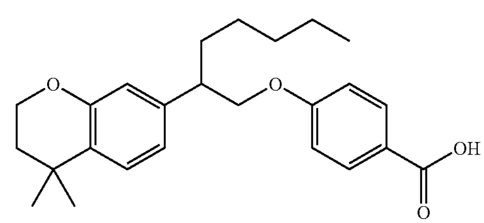 | 3921/ 3162/ 3768 |

-continued

| Example | Structure | Binding IC50 nM α/β/γ |
|---------|-----------|----------------------|
| 5.2 | 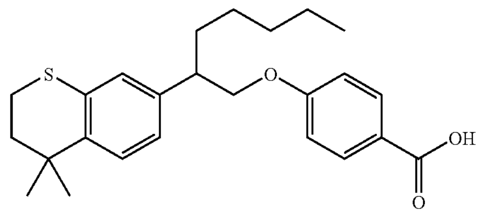 | 2065/ 3005/ 3226 |
| 5.3 | 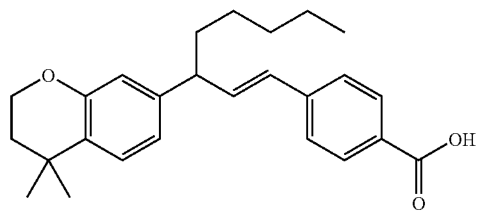 | 6920/ 2919/ 3868 |
| 5.4 | 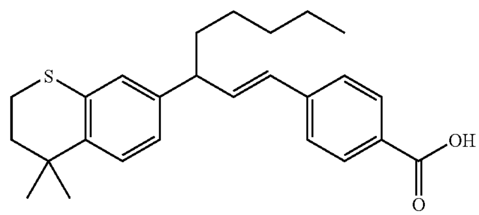 | 1579/ 1487/ 2326 |
| 5.5 | 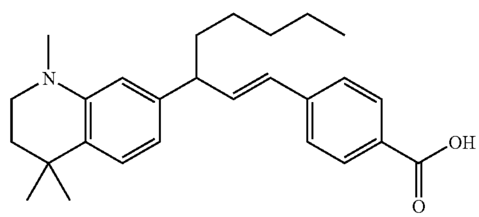 | 1455/ 1938/ 1417 |
| 5.6 | 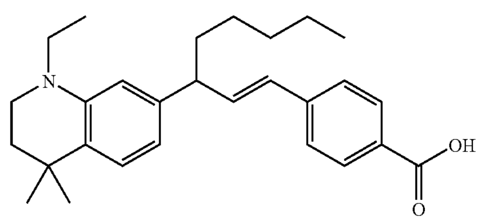 | 1284/ 1474/ 1000 |
| 5.7 | 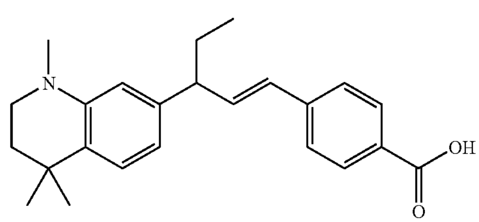 | 3386/ 1053/ >10000 |
| 5.10 | 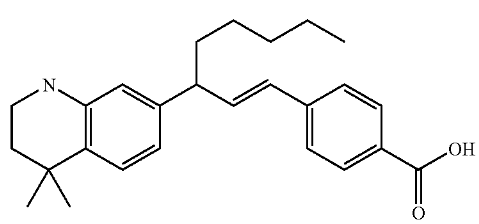 | 5139/ 8272/ 6390 |

-continued

| Example | Structure | Binding IC50 nM α/β/γ |
|---------|-----------|----------------------|
| 5.11 | 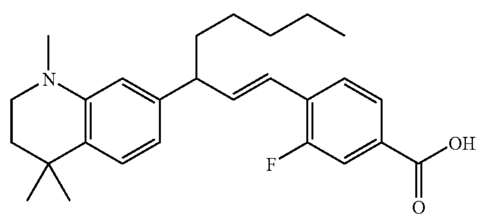 | 6287/ 3263/ 4064 |
| 5.12 | 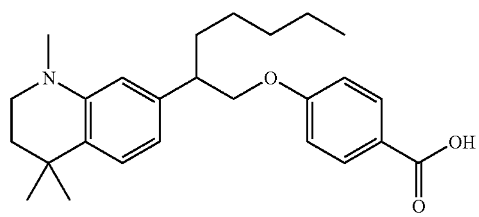 | 3174/ 4146/ 5436 |
| 5.13 | 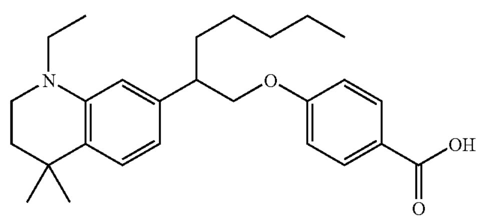 | 2516/ 3125/ 3603 |

Example 6.2

Dermatological and Antitumour Assays

The suitability of the compounds of the invention in treating dermatological disorders caused by light or age and the promotion of wound healing may be determined by methods described in the art (Mustoe et al., *Science* 237, 1333 1987; Sprugel et al., *J. Pathol.*, 129, 601, 1987, which are herein incorporated by reference). Methods described in the art may be used to determine the usefulness of the compounds of the invention to treating dermatological disorders such as acne or psoriasis (Boyd, *Am. J. Med.*, 86, 568, 1989 and references therein; Doran et al., *Methods in Enzymology*, 190, 34, 1990, which are herein incorporated by reference). Finally, the ability of the compounds of the invention to treat cancer may also be determined by methods described in the art (Sporn et al., *Fed. Proc.* 1976, 1332; Hong et al., "Retinoids and Human Cancer" in *The Retinoids: Biology, Chemistry and Medicine*, M. B. Sporn, A. B. Roberts and D. S. Goodman (eds.) Raven Press, New York, 1994, 597-630, which are herein incorporated by reference).

Example 6.3

Measurement of Alveolar Repair in Rat Lung with Compounds of the Invention

Compounds of the invention may be evaluated for their effects on alveolar repair in the rat model of elastase-induced emphysema (Massaro et al., *Nature*, 1997, Vol. 3, No. 6: 675; Massaro et al., U.S. Pat. No. 5,998,486). Preferably, animals are divided into treatment groups of approximately eight. Lung inflammation and alveolar damage may be induced in male Sprague Dawley rats by a single instillation of about 2 U/gram body mass of pancreatic elastase (porcine derived, Calbiochem).

Animals may be treated with a compound of the invention formulated Miglyol at convenient oral dosage ranges (preferably, between about 10.0 mg/kg and 0.0001 mg/kg) and will be dosed orally once per day starting 21 days post injury. Control groups are challenged with elastase and 21 days later are treated with vehicle (Miglyol) for 14 days. Animals were sacrificed 24 hours after the last dose by exsanguination under deep anesthesia. Blood was collected at time of exsanguination for analysis.

The lungs are inflated with 10% neutral buffered formalin by intratracheal instillation at a constant rate (1 ml/gram body mass/min). The lung is excised and immersed in fixative for 24 hours prior to processing. Standard methods were used to prepare 5 µm paraffin sections. Sections were stained with Hematoxylin and Eosin. Alveolar measurements were made in four regions of the lung/rat by Computerized Morphometric analysis. The mean value/treatment group may be determined by summing the average area/rat for all eight rats/treatment groups and repair of elastase damage expressed as percentage of repair relative to the elastase+vehicle treated group from the following calculation:

% Alveolar Repair:

Data is given for, 4-[3-(1,4,4-trimethyl-1,2,3,4-tetrahydro-quinolin-7-yl)-oct-1-enyl]-benzoic acid, Compound 9.

| Dose [µg/kg], p.o. | % Alveolar repair |
|---|---|
| 100 | 60.9 |
| 10 | 54 |
| 1 | 65 |

7. FORMULATION EXAMPLES

Example 7.1

Oral Formulation

Table 2 provides the ingredients for a tablet dosage form of a compound of the invention:

TABLE 2

| Component | Quantity per Tablet (mg) |
|---|---|
| Compound of the invention | 0.1–10.0 |
| Lactose | 125.0 |
| Corn Starch | 50 |
| Magnesium Stearate | 0.5 |
| Croscarmellose Sodium | 25 |

The active ingredient (i.e., a compound of the invention) is blended with the lactose until a uniform mixture is formed. The remaining ingredients are mixed intimately with the lactose mixture and are then pressed into single scored tablets.

Example 7.2

Oral Formulation

Capsules of a compound of the invention suitable for the treatment of emphysema may be made using the ingredients provided in Table 3.

TABLE 3

| Component | Quantity per capsule (mg) |
|---|---|
| Compound of the invention | 0.1–5.0 |
| Lactose | 148 |
| Magnesium Stearate | 2 |

The above ingredients are mixed intimately and loaded into a hard-shell gelatin capsule.

Example 7.3

Suspension Formulation

TABLE 4

| Component | Amount |
|---|---|
| Compound of the invention | 0.1 g–1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |

TABLE 4-continued

| Component | Amount |
|---|---|
| Flavorings | 0.035 ml |
| Colorings | 0.5 mg |
| Distilled water | q.s. to 100 ml |

The above ingredients listed in Table 4 are mixed to form a suspension for oral administration.

Example 7.4

Injectable Formulation

TABLE 5

| Component | Amount |
|---|---|
| Compound of the invention | 0.02 g–0.2 g |
| Sodium acetate buffer solution, 0.4 M | 2.0 ml |
| HCl (1N) or NaOH (1N) | q.s. to suitable pH |
| Distilled water | q.s. to 20 ml |

The above ingredients listed in Table 5 are mixed to form an injectable formulation.

Example 7.5

Injectable Formulation

TABLE 6

| Component | Amount (mg/ml) |
|---|---|
| Compound of the invention | 2.0–20 |
| Citric acid | 0.2 |
| Sodium citrate | 2.6 |
| Benzalkonium chloride | 0.2 |
| Sorbitol | 35 |
| Sodium taurocholate or glycholate | 10 |

The above ingredients are mixed to form an injectable formulation.

Example 7.6

Nasal Formulation

TABLE 7

| Component | Amount |
|---|---|
| Compound of the invention | 0.2 g |
| Sodium acetate buffer solution, 0.4 M | 2.0 ml |
| HCl (1N) or NaOH (1N) | q.s. to suitable pH |
| Distilled or sterile water | q.s to 20 ml |

The above ingredients are mixed to form a suspension for nasal administration.

Example 7.7

Inhalation Formulation

TABLE 8

| Component | Percentage by weight |
|---|---|
| Compound of the invention (stabilized with □α-tocopherol) | 1.0 |
| 1,1,2-tricholoro-trifluoroethane | 26.1 |
| 40% by weight dichlorodifluoromethane and 60% by weight 1,2-dichloro-1,1,2,2 tetraflouroethane | 72.0 |

A compound of the invention is dissolved carefully in 1,1,2-tricholoro-1,2,2 trifluoroethane without evaporation of any solvent and the resultant solution is filtered and stored in a sealed container. The resultant solution and the propellant gas may be introduced into aerosol cans for dispensation in the percentages shown in Table 8 using methods known to the skilled artisan. A metering valve which is designed for a discharge of between 100 μg and 300 μg per spray shot may be employed to deliver the correct dosage of the compound of the invention.

Example 7.8

Inhalation Formulation of a Compound of the Invention

TABLE 9

| Component | Percentage by weight |
|---|---|
| Compound of the invention (stabilized with □α-tocopherol) | 0.5 |
| Emulsifier (i.e., Cremophor RH 40) | 22.0 |
| 1,2 propylene glycol | 2.0 |
| Water and carrier gas | ad 100% by weight |

Cremaphor RH 40 may be purchased from BASF corporation. Other emulsifiers or solutizers are known to those of skill in the art and may be added to the aqueous solvent instead of Cremaphor RH 40. A compound of the invention, emulsifier, 1,2 propylene glycol and water are mixed together to form a solution. The above liquid formulation may be used, for example, in a pressurized gas aerosol with an appropriate carrier gas (e.g., nitrogen or carbon dioxide).

Example 7.9

EHD Formulation of a Compound of the Invention

TABLE 10

| Component | Percentage by weight |
|---|---|
| Compound of the invention (stabilized with □α-tocopherol) | 0.1 |
| Emulsifier (i.e., Cremophor RH 40) | 10.0 |
| Polyethylene glycol | 3.0 |
| Water | 86.9 |

A compound of the invention, emulsifier, polyethylene glycol and water are mixed together to form a solution. The above liquid formulation may be used in typical EHD devices known in the art.

The embodiments of the invention described above are intended to be merely exemplary, and those skilled in the art will recognize, or be able to ascertain using no more than routine experimentation, numerous equivalents to the specific procedures described herein. All such equivalents are considered to be within the scope of the invention and are encompassed by the following claims.

What is claimed is:

1. A method of treating emphysema in a mammal comprising administering to a mammal in need of such treatment a therapeutically effective amount of a compound according to formula (I)

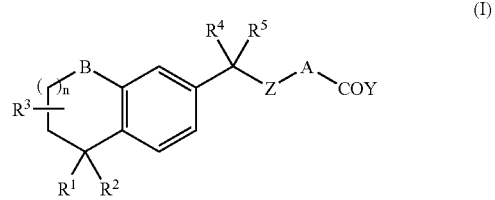

or a pharmaceutically acceptable salt thereof wherein:
n is 1;
A is phenyl;
B is $NR^6$;
$R^6$ is hydrogen or alkyl;
Y is —$OR^7$;
$R^7$ is hydrogen, alkyl, aryl, arylalkyl, cycloalkyl or cycloalkyl-alkyl;
Z is —$C(R^{101})_2O$—, —$R^{102}C=CR^{102}$—, —$C\equiv C$—, —$C(R^{103})_2S$—, —$C(O)O$— or —$C(O)NR^{10}$—;
each of $R^{10}$, $R^{101}$, $R^{102}$ and $R^{103}$ is independently hydrogen or alkyl;
$R^1$ and $R^2$ are independently hydrogen or alkyl;
$R^3$ hydrogen or alkyl; and
$R^4$ and $R^5$ are independently hydrogen, ($C_1$-$C_8$) alkyl or arylalkyl.

2. A method for treating emphysema comprising delivering a formulation of a compound of claim 1 into the lungs of a mammal.

* * * * *